(12) United States Patent
Penhasi et al.

(10) Patent No.: US 10,543,175 B1
(45) Date of Patent: Jan. 28, 2020

(54) FILM COMPOSITION AND METHODS FOR PRODUCING THE SAME

(71) Applicant: DeGama Berrier Ltd., Grand Cayman (KY)

(72) Inventors: Adel Penhasi, Holon (IL); Shiran Alon, Ma'ale Adumim (IL)

( * ) Notice: Subject to any disclaimer, the term of this patent is extended or adjusted under 35 U.S.C. 154(b) by 0 days.

(21) Appl. No.: 14/280,696

(22) Filed: May 19, 2014

Related U.S. Application Data

(60) Provisional application No. 61/824,368, filed on May 17, 2013.

(51) Int. Cl.
| | | |
|---|---|---|
| *A61K 9/48* | (2006.01) | |
| *A61K 9/20* | (2006.01) | |
| *C08K 5/09* | (2006.01) | |
| *C09D 101/28* | (2006.01) | |
| *C09D 171/02* | (2006.01) | |
| *C09D 129/04* | (2006.01) | |

(52) U.S. Cl.
CPC .......... *A61K 9/4816* (2013.01); *A61K 9/2027* (2013.01); *C08K 5/09* (2013.01); *C09D 101/28* (2013.01); *C09D 129/04* (2013.01); *C09D 171/02* (2013.01)

(58) Field of Classification Search
None
See application file for complete search history.

(56) References Cited

U.S. PATENT DOCUMENTS

| | | | |
|---|---|---|---|
| 4,515,769 A | 5/1985 | Merritt et al. | |
| 4,661,359 A * | 4/1987 | Seaborne | A23B 4/10 |
| | | | 426/101 |
| 4,994,279 A | 2/1991 | Aoki et al. | |
| 6,234,464 B1 | 5/2001 | Krumbholz et al. | |
| 6,290,988 B1 | 9/2001 | Van Vilsteren | |
| 6,649,702 B1 * | 11/2003 | Rapoport | A61K 9/0009 |
| | | | 424/486 |
| 6,974,594 B2 | 12/2005 | Ko et al. | |
| 2003/0012819 A1 | 1/2003 | Ko et al. | |
| 2003/0165613 A1 * | 9/2003 | Chappa | A61L 27/34 |
| | | | 427/2.24 |
| 2003/0180362 A1 * | 9/2003 | Park | A61K 9/2077 |
| | | | 424/470 |
| 2004/0121002 A1 | 6/2004 | Lee et al. | |
| 2005/0008610 A1 | 1/2005 | Schwarz et al. | |
| 2005/0019417 A1 | 1/2005 | Ko et al. | |
| 2005/0079197 A1 * | 4/2005 | Kataoka | A61F 2/16 |
| | | | 424/423 |
| 2005/0153018 A1 | 7/2005 | Ubbink et al. | |
| 2005/0266069 A1 | 12/2005 | Simmons et al. | |
| 2006/0029646 A1 | 2/2006 | Vanderkooi | |
| 2006/0034937 A1 | 2/2006 | Patel | |
| 2007/0098847 A1 | 5/2007 | Teissier | |
| 2007/0098854 A1 | 5/2007 | Van Lengerich et al. | |
| 2007/0160589 A1 | 7/2007 | Mattson | |
| 2008/0193485 A1 | 8/2008 | Gorbach et al. | |
| 2009/0092704 A1 | 4/2009 | Gately et al. | |
| 2010/0047400 A1 | 2/2010 | Carlson et al. | |
| 2010/0055083 A1 | 3/2010 | Kowalski et al. | |
| 2010/0055189 A1 * | 3/2010 | Hubbell | A61K 9/0034 |
| | | | 424/489 |
| 2010/0074994 A1 | 3/2010 | Harel et al. | |
| 2010/0189767 A1 | 7/2010 | Shimoni et al. | |

FOREIGN PATENT DOCUMENTS

| | | |
|---|---|---|
| EP | 1010372 A2 | 6/2000 |
| WO | 199400019 A1 | 1/1994 |
| WO | 199608261 A1 | 3/1996 |
| WO | 2004022031 | 3/2004 |
| WO | 2007058614 A1 | 5/2007 |
| WO | 2007100179 A1 | 9/2007 |
| WO | 2008035332 A1 | 3/2008 |
| WO | 2008037578 A1 | 4/2008 |
| WO | 2009069122 A1 | 6/2009 |
| WO | 2009089115 | 7/2009 |
| WO | 2009158368 | 12/2009 |
| WO | 2011004375 | 1/2011 |
| WO | 2012020403 | 2/2012 |

OTHER PUBLICATIONS

Pharmaenfo, obtained online at: http://pharmaenfo.com/Excipients/excipientDetail/Poloxamer, Aug. 14, 2004, pp. 1-9.*
Pluracare, BASF Technical information, Jul. 2009, pp. 1-10.*
Gao et al., Colloids and Surface B: Biointerfaces, 2011, 88, 741-748.*
Zambiazi et al., B.CEPPA, Curitiba, v. 25, n. 1, pp. 111-120. (Year: 2007).*
Pluronic Technical Bulletin, BASF, pp. 1-2. (Year: 2004).*
Talasaz et al., Journal of Applied Polymer Science, 109, pp. 2369-2374. (Year: 2008).*
International Search Report for related PCTIL1100640 dated Dec. 23, 2011.
Examination Report for related AU 2010269814 dated Jan. 16, 2013.
Examination Report for related NZ 597992 dated Jul. 23, 2013.
ISR for PCT/IL2008/001539 dated Jun. 1, 2010.
ISR for PCT/IL2010/000550 dated Nov. 12, 2010.
OA for related CN 201080035882.5 dated Jan. 5, 2013.
Extended SR for EP 10796812.5 dated Jul. 16, 2013.
Anal et al. (2007) Recent advances in microencapsulation of probiotics for industrial applications and targeted delivery; Trends in Food Science & Technology; vol. 18, Issue 5, May 2007, pp. 240-251.
International Search Report for related PCT/IL2012/050533 dated May 12, 2013.
Madene, Atmane, et al. "Flavour encapsulation and controlled release—a review." International journal of food science & technology 41.1 (2006): 1-21.

(Continued)

*Primary Examiner* — Abigail Vanhorn

(57) ABSTRACT

A film composition for coating a pharmaceutical, nutraceutical or nutritional composition comprising a molecular mixture of a hydrophilic film forming polymer having thermo-sensitive sol gel forming properties and having a first lower critical solution temperature (LCST), a hydrophobic fatty component and a micelle-forming block copolymer having a second lower critical solution temperature (LCST) and an HLB value of about 9 to 20, wherein said second LCST is lower than said first LCST.

13 Claims, 14 Drawing Sheets

(56) References Cited

OTHER PUBLICATIONS

Yoshii, Hidefumi, et al. "Flavor release from spray-dried maltodextrin/gum arabic or soy matrices as a function of storage relative humidity." Innovative Food Science & Emerging Technologies 2.1 (2001): 55-61.
International Search Report for related PCT/IB2011/055462 dated May 2, 2012.
Database WPI 1-61 Week 199611 Thomson Scientific, London, GB; AN 1996-103950 XP002672415, & KR 940 004 883 B1 (Hill Glucose co Ltd) Jun. 4, 1994 (Jun. 4, 1994).
Office Action for related CN201180065438 translation dated Jun. 18, 2014.
International Search Report for related PCT/IL2012/050453 dated May 10, 2013.
Evonik: "Technical Information EUDRAGIT L30 D-55", Jan. 1, 2012 (Jan. 1, 2012), XP55040439, Retrieved from the Internet: URL:http://eudragit.evonik.com/product/eudragit/Documents/evonik-specifications-eudragit-l-30-d-55.pdf [retrieved on Oct. 9, 2012].
Fmc Biopolymer: "Material Safety Data Sheet Aquacoat CPD Cellulose Acetate Phthalate Aqueous Dispersion", Jan. 1, 2006 (Jan. 1, 2006), XP55040437, Retrieved from the Internet: URL:http://www.fmcbiopolymer.com/Portals/Pharm/Content/Docs/aquacoatcpdmsds.pdf [retrieved on Oct. 9, 2012].
Dow Chemicals: "Ethocel: Ethylcellulose Polymers Technical Handbook", Sep. 1. 2005 (Sep. 1, 2005), XP55040326, Retrieved from the Internet: URL:http://www.dow.com/dowwolff/en/pdf/192-00818.pdf [retrieved on Oct. 8, 2012].
Colorcon: "Opadry II, Opadry amb", Aug. 1, 2009 (Aug. 1, 2009), XP55040271, Retrieved from the Internet: URL: http://www.colorcon.com/literature/marketing/fc/Opadry II/ads_opadry_II_amb_IRfc_matracices.pdf [retrieved on—Oct. 8, 2012].
Seppic: "Sepifilm LP", Sep. 1, 2004 (Sep. 1, 2004), XP55040273, Retrieved from the Internet: URL:http://abstracts.aapspharmaceutica.com/expoaaps07/Data/EC/Event/Exhibitors/202/2e4a0b37-9255-47c1-8b7f-ffe724b25ee1.pdf [retrieved on Oct. 8, 2012].
International Search Report for related PCT/IB2012/052857 dated Oct. 15, 2012.
International Search Report for related PCT/IL2014/050368 dated Aug. 25, 2014.
Ubbink, J. et al. 2006. Trends in Food Science and Technology. 17: 244-254.

\* cited by examiner

FILM COMPOSITION AND METHODS FOR PRODUCING THE SAME

FIELD OF THE INVENTION

The present invention relates to the fields of pharmaceutical, biomedical, packaging and food, and more particularly, to film compositions for coating pharmaceutical, nutraceutical or nutritional compositions.

BACKGROUND OF THE INVENTION

Protection of pharmaceutical, nutritional and nutraceutical dosage forms from environmental moisture, especially at elevated temperatures is important when the active material is adversely affected by the presence of moisture and/or heat. The negative effects of moisture may occur during common production processes such as processes that involve wet granulation and/or coating. Alternatively, the moisture may damage the active material during storage and negatively affect the shelf life of a final product. Common approaches aimed to limit the damage to the active material, include packaging of the dosage forms containing the moisture sensitive active material in different packaging elements, such as microcapsules, tablets, capsules and the like. However, especially in places where climate is very humid, the special packaging does not provide a complete moisture protection because of the moisture captured inside the above mentioned packaging. Another way to prevent or diminish the damage that may be caused by moisture and to reduce the need for special packaging is to coat the solid dosage forms with materials which have moisture barrier properties. Such materials have essentially a low water vapour permeation (WVP) or a low water vapor transition rate (WVTR). These coatings usually do not affect the basic properties of the dosage forms such as the disintegration time and the release profile of the active material. Examples of moisture sensitive drugs include atorvastatin, ranitidine, temazepam, most vitamins, numerous herbals, unsaturated fatty acids and probiotic bacteria. The damage that may occur due to moisture may include, for example, degradation of active material by hydrolysis, destruction of probiotic bacteria or significant reduction in CFU (colony forming unites) value, changes in the appearance of the dosage form on storage, changes in the disintegration and/or dissolution times of the dosage form. Moisture barrier coatings are thus applied to protect the dosage form from such damages.

In order to achieve a moisture barrier coating, usually a hydrophobic water insoluble polymer is used. The polymers generally employed for this purpose are polyvinyl acetate, zein, shellac, cellulose acetate phthalate (CAP), EUDRAGIT® E 100 which is a cationic copolymer based on dimethylaminoethyl methacrylate, butyl methacrylate, and methyl methacrylate with a ratio of 2:1:1, ethylcellulose (EC) and the like. Such polymers, however, prolong the disintegration of the dosage form in the body after administration and thus delay the release of active materials or probiotic bacteria. Likewise, coating with these polymers necessitates the involvement of use of organic solvent which is not desired because such a process enforces additional expenses relating to air conditioning equipment, anti-explosion provisions, and the like to safely handle such materials. Another way to achieve a moisture barrier coating is a combination of a water soluble polymer with lipophilic substances. The hydrophobic or lipophilic substances particles will be embedded in water soluble film after coating or film formation. Although the presence of lipophilic substance particles in the film may reduce the water vapour transition, they cannot cover all the area of the film, and thus water vapour can still easily penetrate through the spaces between the particles.

BRIEF DESCRIPTION OF THE DRAWINGS

The present invention will become fully understood from the detailed description given herein below and the accompanying drawings, which are given by way of illustration and example only, and thus not limiting in any way, wherein.

SUMMARY OF THE INVENTION

Figure 1:
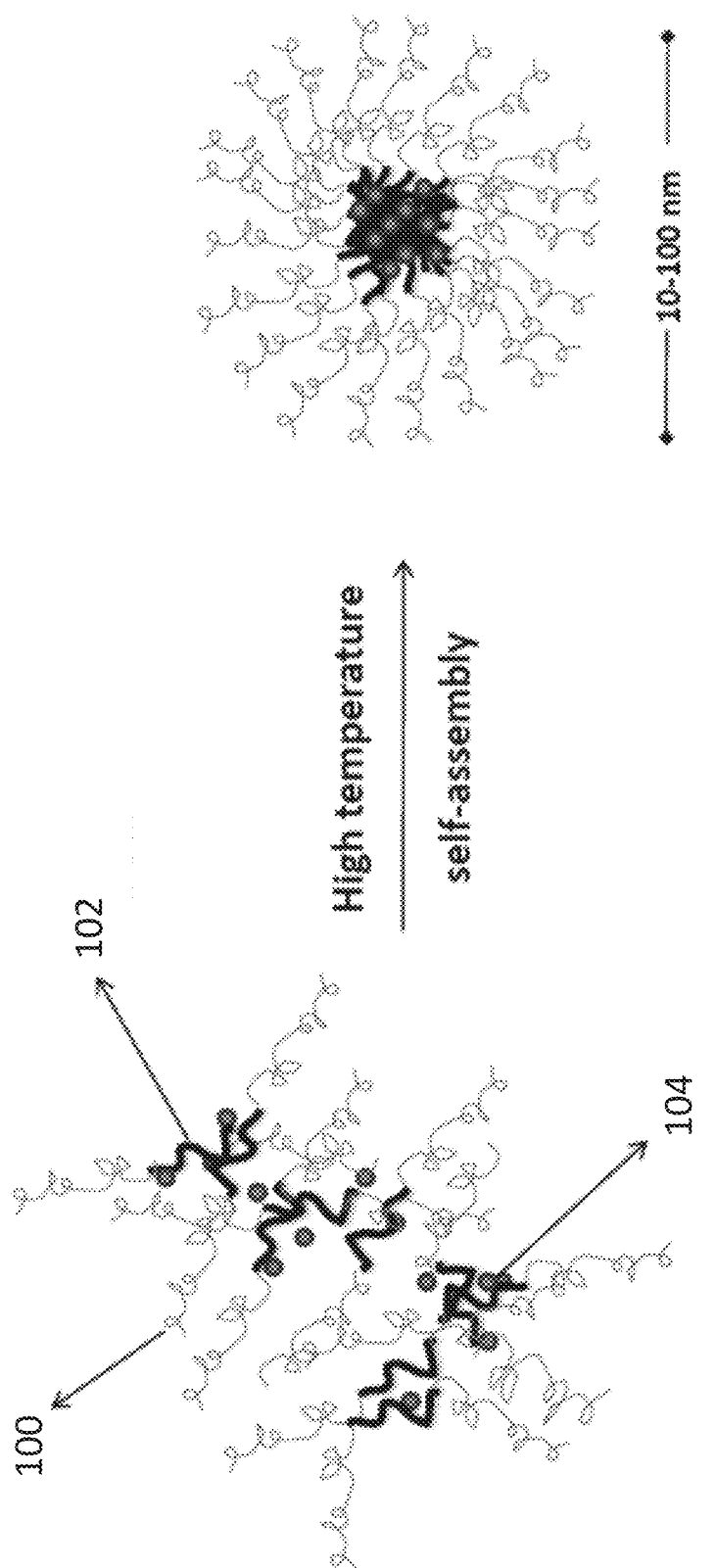
FIG. 1 illustrates a structure of a micelle composed of a micelle-forming block copolymer having a lower critical solution temperature (LCST) and a critical micelle concentration (CMC) in which hydrophobic fatty component has been entrapped.

According to some demonstrative embodiments of the present invention, there is provided a composition of film for coating a pharmaceutical, nutraceutical or nutritional composition. According to some embodiments, the composition of film may contain at least one hydrophilic film forming polymer, at least one hydrophobic fatty component and at least one micelle-forming block copolymer.

In some embodiments, at least one hydrophilic film forming polymer may have a thermo-sensitive sol gel forming properties having a lower critical solution temperature (LCST).

According to some embodiments, the composition of film may have improved moisture barrier properties at ambient and elevated temperatures and thus low water vapour transition rate.

According to some demonstrative embodiments, the composition of film may be used as a coating film for granules, microspheres, pellets, microcapsules, mini-tablets, tablets, caplets and capsules and the like. According to some embodiments, the composition may also be used for microencapsulation for different food products (foodstuffs), nutritional, pharmaceutical and nutraceutical products, e.g., wherein the composition of the present invention may provide the active materials and probiotics of such products with high survival, viability and/or resistance. According to some embodiments, the composition of the present invention may provide the active materials and probiotics with high survival, viability and/or resistance during different processes, e.g., processes which include elevated temperatures, and/or post production, e.g., during storage of the product.

In some demonstrative embodiments, the composition can also be used as degradable packaging material.

According to some embodiments, the present invention also provides for a formulation and method of production of a composition including hydrophilic polymer(s), hydrophobic fatty component(s) and micelle-forming block copolymer(s) for forming a sealing coat, wherein the components of the composition are in such a ratio which will not disrupt the basic and/or mechanical properties of the polymer, e.g., the film forming properties. According to some embodiments, the composition may be based on a blend of the components at molecular level. The present invention relates to a formulation for producing a film for coating solid dosage forms or moisture bather membrane. The formulation comprises at least 1) a hydrophilic film forming polymer having thermo-sensitive sol gel forming properties having a lower critical solution temperature (LCST), 2) at least a hydrophobic fatty component and 3) at least a micelle-forming block copolymer having a lower critical solution temperature (LCST) and a critical micelle concentration (CMC) and an HLB value of about 9 to 18 and whose LCST is higher than that of said hydrophilic film forming polymer, having improved moisture barrier at ambient and elevated temperature and thus low water vapour transition rate. The formulation may include other additives such as glidant, plasticizer flavouring agents, colorant, such as a pigment. and the like. The formulation will be useful for producing either a sprayable dispersion/emulsion or solution for coating on various substrates or film formation for producing membrane.

The present invention also relates to a process for producing the film formulation by either producing a dispersion/emulsion in an aqueous medium or solution in an organic solvent which will be ready for spraying on various substrates such as nutritional, nutraceutical or pharmaceutical active ingredient in a solid dosage form to produce a film coating on the nutritional, nutraceutical or pharmaceutical active ingredient in a solid dosage form or pouring to form a film membrane.

According to some demonstrative embodiments, there is provided a film composition for coating a pharmaceutical, nutraceutical or nutritional composition which may comprise a molecular mixture of at least one hydrophilic film forming polymer having thermo-sensitive sol gel forming properties having a first lower critical solution temperature (LCST); at least one hydrophobic fatty component; and at least one micelle-forming block copolymer, e.g., a micelle-forming block copolymer having a second lower critical solution temperature (LCST) and an HLB value of about 9 to 20. According to some embodiments, the second LCST is higher than said first LCST.

DETAILED DESCRIPTION OF THE INVENTION

According to some demonstrative embodiments, there is provided a film composition for coating a pharmaceutical, nutraceutical or nutritional composition which may comprise a molecular mixture of at least one hydrophilic film forming polymer having thermo-sensitive sol gel forming properties having a first lower critical solution temperature (LCST); at least one hydrophobic fatty component; and at least one micelle-forming block copolymer, e.g., a micelle-forming block copolymer having a second lower critical solution temperature (LCST) and an HLB value of about 9 to 20. According to some embodiments, the second LCST is higher than said first LCST. Reference is made to FIG. 1 which is a schematic illustration of micelles-forming tri-block-copolymer below its lower critical solution temperature (LCST) and the structure of a micelle composed of micelle-forming block copolymer having a lower critical solution temperature (LCST) and a critical micelle concentration (CMC) in which hydrophobic fatty component has been entrapped. Self assembling of triblock copolymers to a micelle structure takes place at high temperature above LCST of the micelles-forming triblock-copolymer.

As shown in FIG. 1, the micelle of the present invention may include a hydrophilic block 100, a hydrophobic block 102 and a hydrophobic fatty component 104.

According to some demonstrative embodiments, the hydrophilic film forming polymer may include one or more of poly-N-substituted acrylamide derivative, polypropyleneoxide, polyvinylmethylether, partially-acetylated product of polyvinyl alcohol, Methylcellulose (MC), hydroxylpropylcellulose (HPC), methylhydroxyethylcelluloce (MHEC), hydroxylpropylmethylcellulose (HPMC), hydroxypropylethylcellulose (HPEC), hydroxymethylpropylcellulose (HMPC), ethylhydroxyethylcellulose (EHEC) (Ethulose), hydroxyethylmethylcellulose (HEMC), hydroxymethylethylcellulose (HMEC), propylhydroxyethylcellulose (PHEC), hydrophobically modified hydroxyethylcellulose (NEXTON), amylose, amylopectin, Poly(organophosphazenes), xyloglucan, synthetic elastin derivative proteins and any of the above polymers further substituted with a hydrophilic or hydrophobic monomer.

According to some embodiments, the poly-N-substituted acrylamide derivative may include one or more of poly(N-isopropylacrylamide) (PNIPAM), Poly-N-acryloylpiperidine, poly(N,N-diethylacrylamide) (PDEAAm), poly(N-vinlycaprolactam) (PVCL), poly[2-(dimethylamino)ethyl methacrylate] (PDMAEMA), poly(ethylene glycol) (PEG), poly(ethylene oxide) (PEO), PEG methacrylate polymers (PEGMA), Poly-N-propylmethacrylamide, Poly-N-isopropylacrylamide Poly-N-diethylacrylamide, Poly-N-isopropylmethacrylamide, Poly-N-cyclopropylacrylamide, Poly-N-acryloylpyrrolidine, Poly-N,N-ethylmethylacrylamide, Poly-N-cyclopropylmethacrylamide, Poly-N-ethylacrylamide, poly-N-substituted methacrylamide derivatives, copolymers comprising an N-substituted acrylamide derivative and an N-substituted methacrylamide derivative, and a copolymer of N-isopropylacrylamide and acrylic acid.

In some demonstrative embodiments, the hydrophilic monomer may include one or more of N-vinyl pyrrolidone, vinylpyridine, acrylamide, methacrylamide, N-methylacrylamide, hydroxyethylmethacrylate, hydroxymethylacrylate, hydroxyethylacrylate, hydroxymethylmethacrylate, methacrylic acid and acrylic acid having an acidic group, and salts of these acids, vinylsulfonic acid, styrenesulfonic acid, derivatives having a basic group such as N,N-dimethylaminoethylmethacrylate, N,N-diethylaminoethyl methacrylate, N,N-dimethylaminopropylacrylamide, and salts of these derivatives.

In some demonstrative embodiments, the hydrophobic monomer may include one or more of ethylacrylate, methylmethacrylate, and glycidylmethacrylate; N-substituted alkymethacrylamide derivatives such as N-n-butylmethacrylamide; vinylchloride, acrylonitrile, styrene, vinyl acetate.

In some demonstrative embodiments, the composition of the present invention may further include a polymer co-network comprising any combination of the above polymers.

In some demonstrative embodiments, the co-networks may include one or more of PNIPAAm and hydroxyethyl methacrylate (HEMA) copolymer, PNIPAAm-co-PHEMA, and NIPAAm with butyl methacrylate (BuMA), P(NIPAAm-co-BuMA), poly(dimethyl acrylamide) (PDMAAm) with Poly(methoxyethyl acrylate), PDMAAm-co-Poly (methoxyethyl acrylate), PNIPAAm hydrogels with polyamino acid crosslinked chains which are thermoresponsive degradable hydrogels, synthesized elastin like polymers with polypeptide repeat units, biodegradable hydrogel comprising thermoresponsive PNIPAAm with cleavable lactic acid and dextran groups, hydrogels of poly(ethylene glycol monomethyl ether methacylate (PEGMA), ABA triblock copolymers of PNIPAAm (block A) and poly(N,N-dimethylacrylamide) (PDMAAm, block B), Conetworks of PNIPAAm, PHEMA and a lactic acid monomer and thermoresponsive cellulose derivatives such as methylcellulose and hydroxypropyl cellulose based hydrogels.

In some demonstrative embodiments, the micelle-forming block copolymer may be present at a concentration that is at least a critical micelle concentration (CMC) of said micelle-forming block copolymer.

In some demonstrative embodiments, the micelle-forming block copolymer may include one or more of amphiphilic di-block (hydrophilic-hydrophobic) or tri-block (hydrophilic-hydrophobic-hydrophilic) polymers, and/or graft (hydrophilic-g-hydrophobic) or ionic (hydrophilic-ionic) copolymers.

In some demonstrative embodiments, the micelle-forming block copolymer may include one or more of a PEO-PPO-PEO block copolymer, AP-A nonionic triblock copolymers composed of a central hydrophobic chain of polyoxypropylene (poly(propylene oxide)) flanked by two hydrophilic chains of polyoxyethylene (poly(ethylene oxide)).

Examples of such copolymers may include poloxamer block copolymer series (such as; Poloxamer 124, Poloxamer 188, Poloxamer 237, Poloxamer 338, and Poloxamer 407, wherein the molecular weight of the polyethylene oxide part may be 1200, 1800, 2250, 3250 and 4000 respectively and wherein the molecular weight of the block copolymers may be 4000, 6000, 8000, 10000 and 12000 respectively.

In some demonstrative embodiments, the micelle-forming block copolymer may include one or more of a EO-PO-EO block copolymers, di-blocks of EO-PO and EO-B and tri-block versions, PO-EO-PO and BO-EO-BO (BO is butylene oxide) DG note—I need more explanation about these copolymers and also a list of examples AP: This is a block copolymer based on polybuthylene glycol or polybuthylene oxide (BO), poly (propylene oxide)-poly (ethylene oxide)-poly (propylene oxide) triblock copolymers (PPO-PEO-PPO), poly (butylene oxide)-poly (ethylene oxide)-(butylene oxide) triblock copolymers (PBO-EO-PBO), poly (ethylene oxide)-poly (butylene oxide)-poly (ethylene oxide) triblock copolymers (PEO-PBO-PEO), Poly(ethylene oxide)-Poly(butylene oxide) diblock copolymer, Poly(ethylene oxide)-Poly(propylene oxide) diblock copolymer, Poly (ethylene-alt-propylene)-poly(ethylene oxide) diblock copolymer, poly(ethylene oxide)-poly(styrene) diblock copolymer, poly(ethylene oxide)-poly(D,L-lactide) diblock copolymer, poly(ethylene oxide)-poly(ε-caprolactone) diblock copolymer, poly(ethylene oxide)-poly(hydrocarbon chain) diblock copolymer, poly(styrene)-poly(vinylpyridine) block copolymers, Poly(ethylene oxide) poly(ethyelene imine) block copolymers, Poly(styrene)-poly(vinyleriphenylphosphine), block copolymers of polyamino acid-PEO copolymers with hydrophobic blocks of aspartic acid and aspartate derivatives, polylysine, polycaprolactone, and poly(lactide), polication-PEO copolymers containing, e.g., poly(ethyleneimine), ionic block copolymers such as polystyrene(PS)-b-polyacrylic acid (PAA), polystyrene(PS)-b-poly(methacrylic acid) (PMA), poly(styrene)-poly(ethylene-propylene) (PS-PEP) diblock and triblock copolymers, poly(styrene)-b-poly(ethylene-butylene) (PS-PEB) diblock and triblock copolymers, poly(styrene)-b-poly(t-butylstyrene) (PS-PtBS) diblock and triblock copolymers, poly (styrene)-poly(hydrogenated polybutadiene)-poly(styrene) (PS-PHB-PS) triblock copolymers, poly(styrene)-poly(isoprene)-poly(styrene) PS-PI-PS triblock copolymers, poly (styrene)-poly (1,1-dihydroperfluorooctyl acrylate) (PS-PFOA), block copolymers of triblock polyalkylene oxide such as poly(dimethylsiloxane)-polyalkylene oxide block copolymers, poly(vinyl acetate)-poly(1,1-dihydroperfluorooctyl acrylate) block copolymers, polycarbolactone-polyethylene glycol polycarbolactone(PCL-PEG-PCL) triblock copolymer, poly(ethylene glycol)-diblock-polycaprolactone (PEG-b-PCL) copolymer, 1,2-distearoyl-phosphatidyl ethanolamine-PEG (2000) (DSPE-PEG2000), poly(ethylene oxide)-block-poly(N-hexyl-Laspartamide) (PEO-b-p(N-HA), poly(ethylene glycol)-poly(aspartic acid) (PEG-P[Asp (ADR)]), PEG-block-poly(N-hexyl stearate L-aspartamide) (PEG-b-PHSA), poly(DL-lactide-co-2-methyl-2-carboxytrimethylene carbonate)-graft-PEG (poly(LA-co-TMCC)-g-PEG), PEG-poly(benzyl aspartate) block-copolymer, PEG-block poly(glutamic acid) PEG-b-poly(Glu), polysorbates (Tween) such as Polysorbate 20 (Polyoxyethylene and sorbitan monolaurate), Polysorbate 40 (Polyoxyethylene and sorbitan monopalmitate), Polysorbate 60 (Polyoxyethylene and sorbitan monostearate), Polysorbate 80 (Polyoxyethylene and sorbitan monooleate), Polyoxyethylene and sorbitan tristearate, poly-d,l-lactide-coglycolide(PLGA) and polyethylene glycol block copolymer.

In some demonstrative embodiments, the hydrophobic fatty component may include one or more of alkene chains, alkane chains, waxes, esters, fatty acids, alcohols, and glycols.

In some demonstrative embodiments, the alkene chains may include paraffin wax.

In some demonstrative embodiments, the waxes may include one or more of bee wax, carnauba wax, japan wax, bone wax, paraffin wax, chinese wax, lanolin (wool wax), shellac wax, spermaceti, bayberry wax, candelilla wax, castor wax, esparto wax, jojoba oil, ouricury wax, rice bran wax, soy wax, ceresin waxes, montan wax, ozocerite, peat waxes, microcrystalline wax, petroleum jelly, polyethylene waxes, fischer-tropsch waxes, chemically modified waxes, substituted amide waxes; polymerized α-olefins; hydrogenated vegetable oil, hydrogenated castor oil; fatty acids, such as lauric acid, myristic acid, palmitic acid, palmitate, palmitoleate, hydroxypalmitate, stearic acid, arachidic acid, oleic acid, stearic acid, behenic acid, sodium stearat, calcium stearate, magnesiu stearate, hydroxyoctacosanyl hydroxystearate, oleate esters of long-chain, esters of fatty acids, fatty alcohols, esterified fatty diols, hydroxylated fatty acid, hydrogenated fatty acid (saturated or partially saturated fatty acids), aliphatic alcohols, phospholipids, lecithin, phosphathydil cholin, triesters of fatty acids for example triglycerides received from fatty acids and glycerol (1,2,3-trihydroxypropane) including fats and oils such as coconut oil, hydrogenated coconut oil, cacao butter (also called *Theobroma* oil or *Theobroma cacao*); fatty acid eutectics.

According to some demonstrative embodiments of the present invention, there is provided a method for preparing the composition as described herein including to preparing a core containing a pharmaceutical, nutraceutical and/or nutritional composition; combining a hydrophobic fatty component and a micelle-forming block copolymer in a solution, suspension or dispersion; adding a hydrophilic film forming polymer to the solution, suspension or dispersion to form a coating; and coating the core with said coating.

In some demonstrative embodiments, combining the hydrophobic fatty component and the micelle-forming block copolymer may take place in a solution, suspension or dispersion and may include melting the hydrophobic fatty component and the micelle-forming block copolymer together.

In some demonstrative embodiments, the temperature of the melting may be above the first LCST.

In some demonstrative embodiments, combining the hydrophobic fatty component and the micelle-forming block copolymer in a solution, suspension or dispersion may include combining the hydrophobic fatty component and the micelle-forming block copolymer together with an organic solvent or with oil.

In some demonstrative embodiments, adding the hydrophilic film forming polymer to the solution, suspension or dispersion to form said coating may be performed at a temperature above said first LCST.

In some demonstrative embodiments, the pharmaceutical, nutraceutical or nutritional composition described herein may include a core and the film composition of the present invention coating the core.

In some demonstrative embodiments, the core may include granules, microspheres, pellets, microcapsules, mini-tablets, tablets, caplets, capsules and the like.

In some demonstrative embodiments of the present invention, there is provided a film composition for coating a pharmaceutical, nutraceutical and nutritional, composition comprising a molecular mixture of a Poloxamer, a fatty acid and HPC.

In some demonstrative embodiments of the present invention, there is provided a film composition for coating a pharmaceutical, nutraceutical and nutritional composition wherein the film composition may include a molecular mixture of a polysorbate (Tween), a fatty acid and HPC.

In some demonstrative embodiments of the present invention, there is provided a pharmaceutical nutraceutical or nutritional composition that may include a core comprising an active ingredient, and a coating layered over the core.

According to some embodiments, the coating may include a molecular mixture of Poloxamer, a fatty acid and HPC.

In some demonstrative embodiments of the present invention, there is provided a pharmaceutical, nutraceutical or nutritional composition that may include core comprising an active ingredient, and a coating layered over said core, said coating comprising a molecular mixture of a polysorbate (Tween), a fatty acid and HPC.

It should be noted that throughout the present disclosure, the invention is described using the text and related drawings. The equations are included only as a possible help to persons skilled in the art, and should not be considered as limiting the invention in any way. Various other equations may be used by persons skilled in the art.

According to some demonstrative embodiments of the present invention there is provided a use of one or more compositions based on a combination of at least two of the following: a hydrophilic film forming polymer having thermo-sensitive sol gel forming properties having a lower critical solution temperature (LCST); at least a hydrophobic fatty component and/or at least a micelle-forming block copolymer having a lower critical solution temperature (LCST) and a critical micelle concentration (CMC) and an HLB value of about 9 to 20 and whose LCST is higher than that of said hydrophilic film forming polymer, results in a remarkable decrease in the water vapour permeation through the film and significant increase in barrier properties of the resulting film coating. According to some embodiments, the composition according to the present invention may be based on a physically blended of components, e.g., in a molecular level, for achieving sealing properties. According to some embodiments, these properties may be achieved by filling inter chains micro-voids existing in hydrophilic film forming polymer which are responsible for penetration of moisture specially at high temperatures by micelles in which the hydrophobic fatty component is entrapped (FIG. 1). The micelles are also responsible for a more stable and tighter connection between hydrophilic film forming polymer and hydrophobic fatty component.

Permeation and Water Vapour Transition Rate (Wvtr)

Permeation describes the transfer of gases and vapours in barrier materials such as polymeric plastics. The process involves:

(1) dissolving the penetrant in the barrier material, (2) diffusion of dissolved penetrant through the material as a result of the concentration gradient, and (3) evaporation of the penetrant from the opposite side of the material (Desorption from the surface of the material).

In general permeation indicates a polymer's ability to transmit liquids, gases, and vapours.

Permeation is generally regarded as an important consideration in determining the performance of plastics or composites, and for good reason. All polymers are generally permeable, and structures such as dual laminates or sheet linings are essentially freestanding polymeric materials.

The transport rate for water vapour is much faster compared to the other components even though the polymer can be a hydrophobic material. The permeability coefficient of a material is an intrinsic material property, since it gives a measure for the amount of gas permeating per second through a material with a surface area of 1 cm² and a thickness of 1 cm normalized for the driving force in cm·Hg. The total amount of gas permeating is expressed as a flux of gas at standard temperature and pressure ($cm^3(STP)/(cm^2/s)$):

$$J=(P/l)(f_{i,feed}-f_{i,permeate})$$

with P the permeability (Barrer=1 10-10 cm3 cm/(cm² s cmHg)), l the membrane thickness (cm), $f_{i,feed}$ and $f_{i,permeate}$ the fugacities of component i on the high pressure side (feed) and low pressure side (permeate) (cmHg), respectively. For low pressure applications the fugacities equal the partial pressure. The permeability of a gas, vapor or liquid through a dense polymeric membrane can be described by the solution-diffusion model equating the permeability P to the product of the diffusivity and solubility:

$$P = D \cdot S$$

where D is the diffusion coefficient (cm2/s) and S the solubility coefficient (cm³(STP)/(cm³ cmHg)). The magnitude of the permeability is determined by the diffusion rate (D), which is a kinetic parameter, and the solubility, a thermodynamic parameter accounting for the amount sorbed by the membrane. The combination of a high mobility for water (diffusivity) and a high solubility causes a high permeability for water compared to other penetrants.

Permeation involves a combination of physical and chemical factors. In general increasing permeant concentration, temperature, pressure, permeant/polymer chem. Similarity, free volumes and voids in polymer may increase the rate of permeation and inversely increasing permeant size/shape, polymer thickness, polymer crystallinity, polymer chain stiffness and polymer inter-chain forces decreases the rate of permeation. Likewise in crystalline polymers, orientation will reduce permeability. Moisture sensitivity may also affect permeability for example some polymers are plasticized by water, causing their permeability to increase. Cross-linking can also affect permeation. The higher the cross linking degree is, the higher the moisture barrier of the membrane. Molecular weight and chemical nature (hydrophilic, hydrophobic) of the polymer are also key factors for permeability.

Water Vapor Transmission Rate (WVTR) is the rate at which water vapor will pass through a material under specified conditions and specimen geometry. This article provides an overview of ASTM F1249.

The basic mathematical treatment of WVTR starts with Fick's first law;

$$J = D \, dc/dx$$

Where J=flux which is the diffusion flow through unite area of film, D=diffusion coefficient, c=concentration of penetrante and x=the distance of the point from the the film surface.

According to Henry's law $C = S \cdot P$ where S=solubility coefficient and P=partial pressure of penetrante. Therefore WVTR equation will be as follows;

$$J = D(C_1 - C_0)/l = D \cdot S(p_1 - p_0)/l$$

$$WVTR = P(\Delta p)/l$$

l=film thickness (m); Δp=water vapor pressure gradient between the two sides of the film (Pa); P=film permeability (g·m-2·s-1 Pa-1).

The permeability of the membrane is determined from the amount or rate of permeation and experimental parameters such as time, sample area, sample thickness, pressure difference, concentrations, etc. the permeability of the membrane can be calculated.

Figure 2:
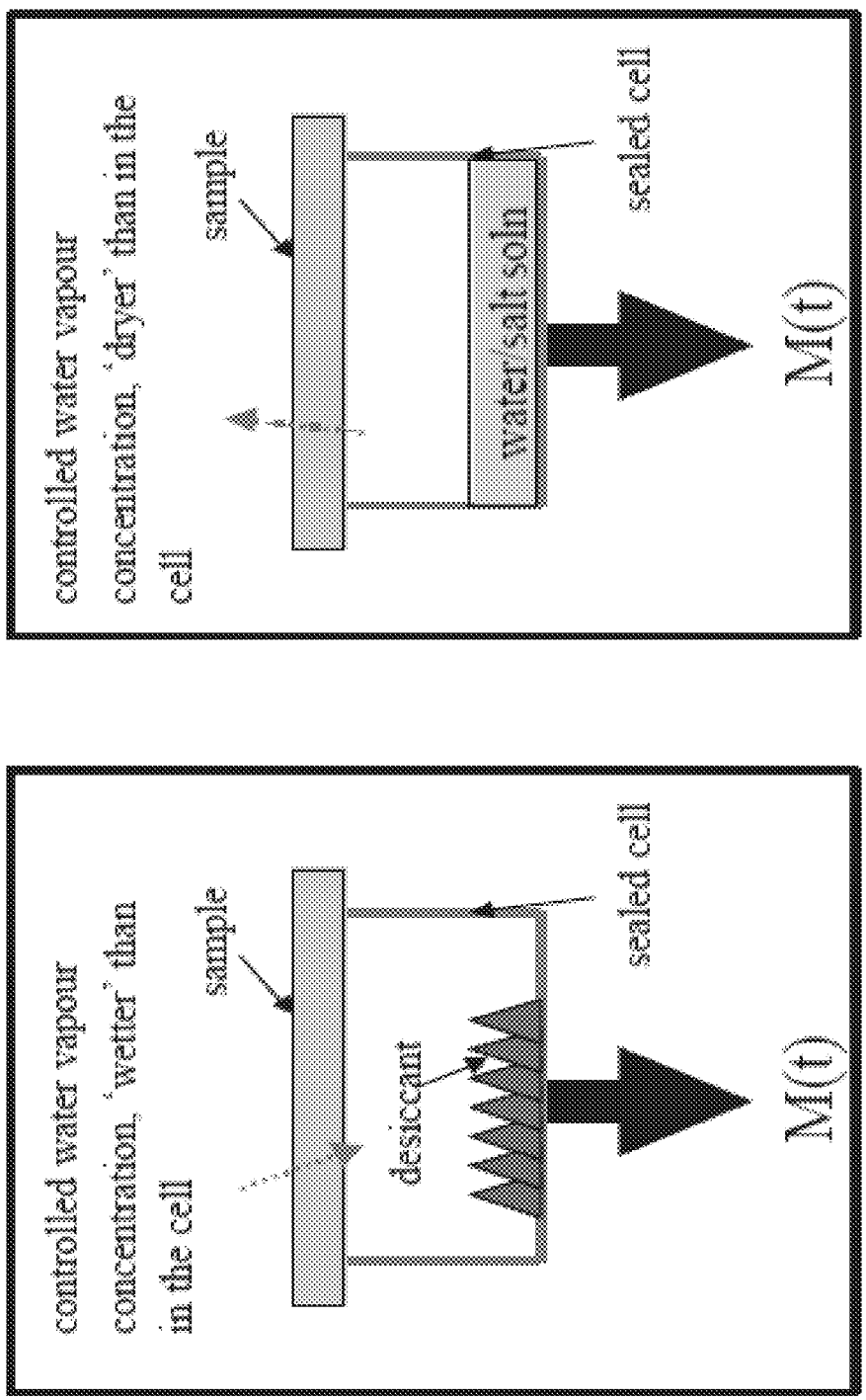
FIG. 2 illustrates dry and wet cup methods for gravimetric Water Vapor Transmission Rate (WVTR) measurement—ASTM E398 Method (Standard Test Method for Water Vapor Transmission Rate of Sheet Materials Using Dynamic Relative Humidity Measurement).

Reference is now made to FIG. 2 Schematic illustration of dry and wet cup methods for gravimetric water vapor transmission rate (WVTR) measurement according to Standard Test Method (ASTM E398 Method), wherein said standard test method for water vapor transmission rate of sheet materials utilizes dynamic relative humidity (RH) measurement.

Figure 3:
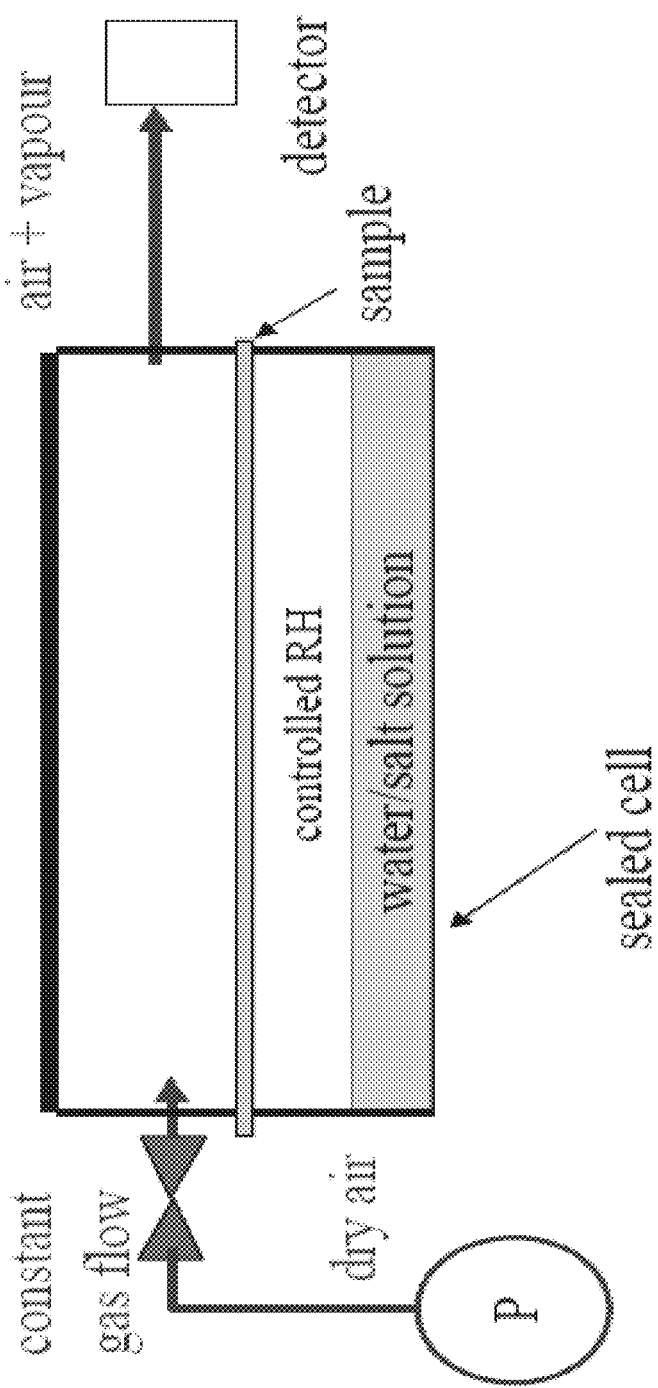
FIG. 3 illustrates a Water Vapor Transmission Rate (WVTR) technique using an IR detector.

Reference is now made to FIG. 3 which illustrates a Water Vapor Transmission Rate (WVTR) technique using an IR detector. As shown in FIG. 3, a sample film is placed in a sealed cell containing a water/salt solution having a controlled RH. A constant gas flow (dry air) is pumped through the sealed cell whereas the air and/or vapor coming out of the sealed cell is examined via a detector, e.g., an Infra-Red (IR) detector, to examine the magnitude of the permeability of the sample.

Free Volume and Voids in Polymer Films

Free volume is an intrinsic property of the polymer matrix and arises from the gaps left between entangled polymer chains. Since the gaps are at the molecular scale, it is not possible to directly observe free volume. Free volume can be thought of as extremely small-scale porosity but free volume pores are dynamic and transient in nature since the size (and existence) of any individual free volume 'pore' depends on the vibrations and transitions of the surrounding polymer chains. The transition of the polymer chains can open and close 'pores' and open/close channels between pores, providing 'pathways' for diffusion jumps.

The absorption and diffusion of molecules in polymer films will depend to a considerable extent on the available free volume within the polymer. The greater the free volume is, the higher the capacity for absorption and the higher the mobility of the molecules within matrix.

Free volume depends on the density and physical state of the polymer. Voids are on a larger size scale than free volume and are 'permanent' features, independent of polymer chain motion.

Voids tend to result from the generation of 'defects', e.g. included air, arising during processing but can also be generated in service (e.g. stress generated crazing or chemical swelling). The volume fraction of voids in a sample will depend on the imposed stress state. Voids, like free volume, offer sites into which molecules can absorb and are far less of a barrier to transport than solid polymer. Voids may also provide sites into which liquids and vapors can condense and thereby dramatically increase their uptake. A high level of void will increase permeability through increasing both the solubility and the effective diffusion coefficient. If voids are linked (open voids), then diffusion rates through these channels will be lead to very much greater permeation than if the voids are isolated (closed voids). The latter can specially happen under effect of temperature.

The Effect of Temperature

Temperature has an effect on the permeability and diffusion properties of small molecules in polymers. Permeability increases about 5% per degree Celsius rise in temperature by increasing free volumes and voids. As the temperature increases, the mobility of the molecular chains increases and thermal expansion leads to a reduced density. Therefore, the free volume in the system will increase, leading to an increased solubility.

Absorption and diffusion normally follow Arrhenius behavior.

Thermo-Sensitive Sol-Gel Forming Polymer

Figure 4:
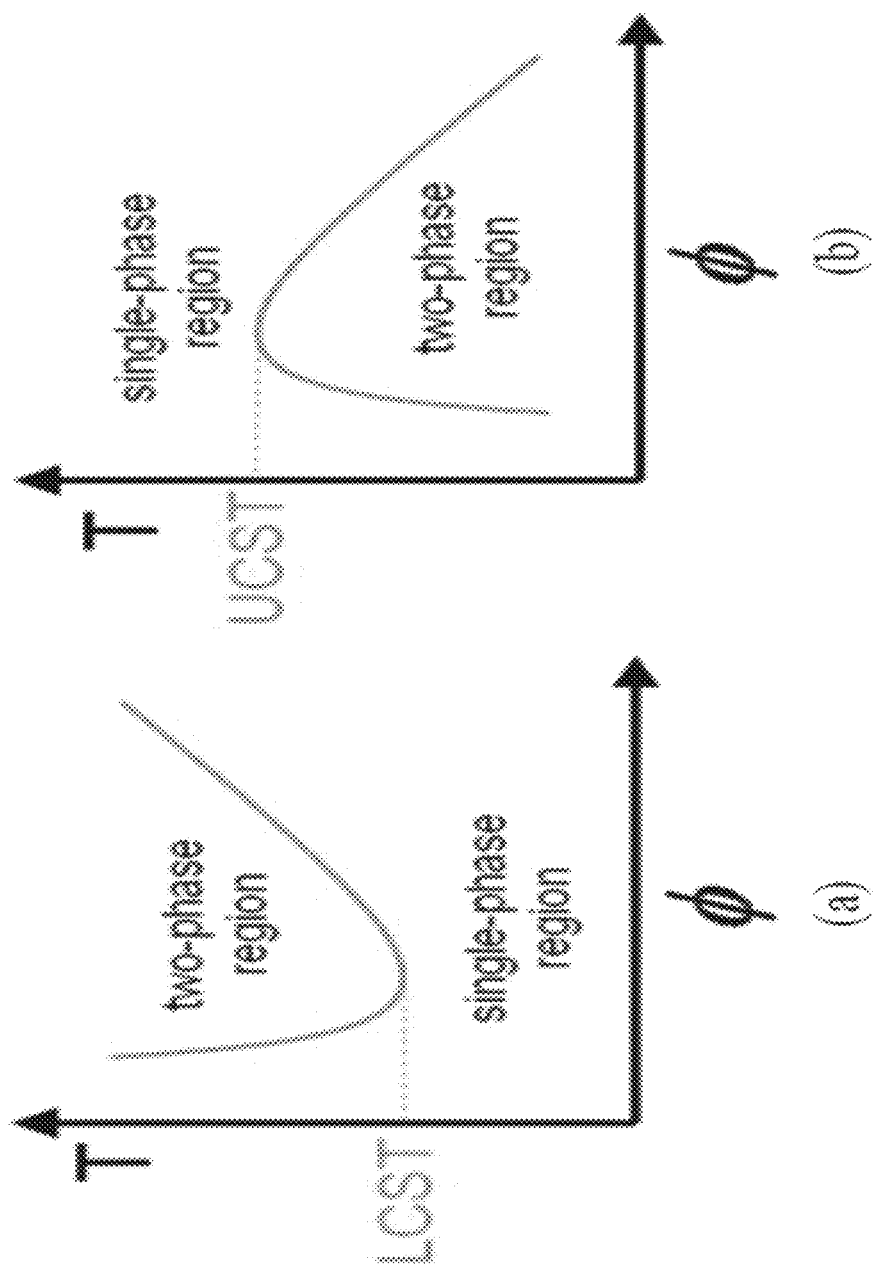
FIG. 4 illustrates phase diagram graphs (a) and (b) depicting lower critical solution temperature (LCST) behavior and upper critical solution temperature (UCST) behavior, respectively, according to some demonstrative embodiments described herein.

Thermosensitive sol gel forming polymers belong to a general group of polymers, smart polymers, which are materials that have the ability to respond to external stimuli. Thermosensitive sol gel forming polymers are those polymers which respond to temperature and change their state under effect of temperature. Basically, There are two main types of thermoresponsive polymers; the first present a lower critical solution temperature (LCST) while the second present an upper critical solution temperature (UCST). LCST and UCST are the respective critical temperature points below and above which the polymer and solvent are completely miscible (for example, as shown in FIG. 4.) Thus, for example, a polymer solution below the LCST is a clear, homogeneous solution while a polymer solution above the LCST appears cloudy (leading to LCST also being referred to as cloud point). This happens because it is energetically more favorable. In particular, considering the free energy of the system using the Gibbs equation $\Delta G = \Delta H - T\Delta S$ (G: Gibbs free energy, H: enthalpy and S: entropy) the reason that phase separation is more favorable when increasing the temperature is mostly due to the entropy of the system. Specifically, the main driving force is the entropy of the water, that when the polymer is not in solution the water is less ordered and has a higher entropy. This is also called the "hydrophobic effect". It is noteworthy that LCST is an entropically driven effect while UCST is an enthalpically driven effect. Above LCST polymer association, chain-chain interactions (hydrophobic effects) and water-water interaction (hydrogen bonding) are dominate over chain-water hydrogen bonding. On the other hand upon decreasing temperature below a critical temperature, LCST, water hydrogen bonding dominates over chain-chain interactions thus the dissolution of the polymer may occur. Macroscopic response of the polymer will depend on the physical state of the chains. If the macromolecular chains are linear and solubilized, the solution will change from mono-phasic to bi-phasic due to polymer precipitation when the transition occurs. Polymer solution is a free-flowing liquid at ambient temperature and gels at high temperature. In some cases, if lowering the amount of thermo-gelling polymer is necessary, it may be blended with a pH-sensitive reversibly gelling polymer.

Reference is now made to FIG. 4 illustrates phase diagram graphs (a) and (b) depicting lower critical solution temperature (LCST) behavior and upper critical solution temperature (UCST) behavior, respectively, according to some demonstrative embodiments described herein As shown in FIG. 4 phase diagrams (a) and (b) examine temperature in axis y vs. polymer volume fraction in axis x. Phase diagram (a) demonstrates the lower critical solution temperature (LCST) behavior and Phase diagram (b) demonstrates the upper critical solution temperature (UCST) behavior. According to some demonstrative embodiments, LCST and UCST are the respective critical temperature points below and above which, respectively, the polymer and solvent are essentially completely miscible. For example, referring to graph (a), a polymer solution below the LCST would be a clear, homogeneous solution while a polymer solution above the LCST appears cloudy (LCST is also sometimes referred to as cloud point).

According to another example, referring to graph (b), a polymer solution above the UCST would be a clear, homogeneous solution while a polymer solution below the UCST appears cloudy.

According to some demonstrative embodiments, the LCST of a thermosensitive sol gel forming polymer may generally be dependent on molecular weight and architecture.

Thermosensitive sol gel forming polymers used as film forming polymer according to the present invention are preferably those that present an LCST. Examples of the thermo-sensitive polymers exhibiting thermally-driven phase transitions according to the present invention may include, but not limited to poly-N-substituted acrylamide derivatives such as for example poly(N-isopropylacrylamide) (PNIPAM), Poly-N-acryloylpiperidine, poly(N,N-diethylacrylamide) (PDEAAm) with an LCST over the range of 25 to 32° C., poly(N-vinlycaprolactam) (PVCL) with an LCST between 25 and 35° C., poly[2-(dimethylamino)ethyl methacrylate] (PDMAEMA) with an LCST of around 50° C., poly(ethylene glycol) (PEG), also called poly(ethylene oxide) (PEO) whose LCST is around 85° C., PEG methacrylate polymers (PEGMA), having a side-PEG chain of 2-10 ethylene oxide units (EO)<10 present a lower critical solution temperature (LCST) that varies depending on the length of the EO side chain, Poly-N-propylmethacrylamide, Poly-N-isopropylacrylamide Poly-N-diethylacrylamide, Poly-N-isopropylmethacrylamide, Poly-N-cyclopropylacrylamide, Poly-N-acryloylpyrrolidine, Poly-N,N-ethylmethylacrylamide, Poly-N-cyclopropylmethacrylamide, Poly-N-ethylacrylamide, poly-N-substituted methacrylamide derivatives, copolymers comprising an N-substituted acrylamide derivative and an N-substituted methacrylamide derivative, copolymer of N-isopropylacrylamide and acrylic acid, polypropyleneoxide, polyvinylmethylether, partially-acetylated product of polyvinyl alcohol, Methylcellulose (MC), hydroxylpropylcellulose (HPC), methylhydroxyethylcelluloce (MHEC), hydroxylpropylmethylcellulose (HPMC), hydroxypropylethylcellulose (HPEC), hydroxymethylpropylcellulose (HMPC), ethylhydroxyethylcellulose (EHEC) (Ethulose), hydroxyethylmethylcellulose (HEMC), hydroxymethylethylcellulose (HMEC), propylhydroxyethylcellulose (PHEC), hydrophobically modified hydroxyethylcellulose (NEXTON), amylose, amylopectin, Poly(organophosphazenes), natural polymers like xyloglucan, Elastin (which is a thermoresponsive polypeptide which has unique thermoresponsive ability. Below its transition temperature it is solvated and extended in solution, however, above its LCST of 30° C., the chains fold) and a mixture thereof.

The most common of these is poly(N-isopropylacrylamide) (PNIPAAm) which has a lower critical solution temperature, LCST of around 32° C. Adjustment of the LCST of PNIPAAm has been achieved by copolymerizing with hydrophilic or hydrophobic monomers rendering the overall hydrophilicity of the polymer higher or lower respectively. According to some embodiments, the above mentioned poly-N-substituted acrylamide derivatives may be either a homopolymer or a copolymer comprising a monomer constituting the above polymer and "another monomer". The "another monomer" may be a hydrophilic monomer, or a hydrophobic monomer. According to some embodiments, when copolymerization with a hydrophilic monomer is conducted, the resultant cloud point temperature may be increased. According to other embodiments, when copolymerization with a hydrophobic monomer is conducted, the resultant cloud point temperature may be decreased. Accordingly, a polymer having a desired cloud point (e.g., a cloud point of higher than 30° C.), may be obtained by selecting monomers to be used for copolymerization. Examples of the above hydrophilic monomers may include: N-vinyl pyrrolidone, vinylpyridine, acrylamide, methacrylamide, N-methylacrylamide, hydroxyethylmethacrylate, hydroxymethylacrylate, hydroxyethylacrylate, hydroxymethylmethacrylate, methacrylic acid and acrylic acid having an acidic group, and salts of these acids, vinylsulfonic acid, styrenesulfonic acid, etc., and derivatives having a basic group such as N,N-dimethylaminoethylmethacrylate, N,N-diethylaminoethyl methacrylate, N,N-dimethylaminopropylacrylamide, salts of these derivatives, etc. However, the hydrophilic monomer of the present invention is not restricted to these specific examples. Examples of the above hydrophobic monomer may include acrylate derivatives and methacrylate derivatives such as ethylacrylate, methylmethacrylate, and glycidylmethacrylate; N-substituted alkymethacrylamide derivatives such as N-n-butyl-methacrylamide; vinylchloride, acrylonitrile, styrene, vinyl acetate, etc. However, the hydrophobic monomer of the present invention is not restricted to these specific examples. Another example of a thermo-sensitive polymers according to some embodiments of the present invention is an etherified cellulose represented by methylcellulose, hydroxypropylcellulose, etc., where the sol-gel transition temperature thereof is as high as about 45° C. or higher. Hydroxypropylcellulose (HPC) is an example of a thermo-sensitive polymer. HPC is an ether of cellulose in which some of the hydroxyl groups in the repeating glucose units have been hydroxypropylated forming —OCH2CH(OH)CH3 groups using propylene oxide. The average number of substituted hydroxyl groups per glucose unit is referred to as the degree of substitution (DS). Complete substitution would provide a DS of 3. Because the hydroxypropyl group added contains a hydroxyl group, this can also be etherified during preparation of HPC. When this occurs, the number of moles of hydroxypropyl groups per glucose ring, moles of substitution (MS), can be higher than 3. Since hydroxypropyl cellulose (HPC) has a combination of hydrophobic and hydrophilic groups, so it also has a lower critical solution temperature (LCST) at 45° C. At temperatures below the LCST, HPC is readily soluble in water; above the LCST, HPC is not soluble.

Thermosensitive sol gel forming polymers used as film forming polymer according to the present invention may also be a hydrogel. Hydrogels are 3-dimensional polymeric networks. There are two main types of gels: physical gels and covalently linked gels. The latter are based on polymer chains that are linked together through covalent bonds at points that are called crosslinks. This type of gels may also be referred to as crosslinked gels or covalently linked networks. Physical gels, according to other embodiments, may be formed by the physical entanglement of polymer chains and/or micelle ordering in solution and not from covalently linked polymer chains. Both of these gels, crosslinked or physical, have the ability to swell in a solvent depending on their compatibility with the solvent. However one of the differences between physical gels and crosslinked gels is that when a physical gel is in the appropriate solvent and it is given enough time and space it will dissolve in the solvent, whereas crosslinked gels will not.

Hydrogels are polymer networks dispersed in water which form semi solid states containing at least of 99% water w/w to polymer. These gels can be either covalently linked polymer networks or physical gels mentioned above. With reference to thermoresponsive polymers, covalently linked networks exhibit a change in their degree of swelling in response to temperature, whereas physical gels show a sol-gel transition.

Figure 5:
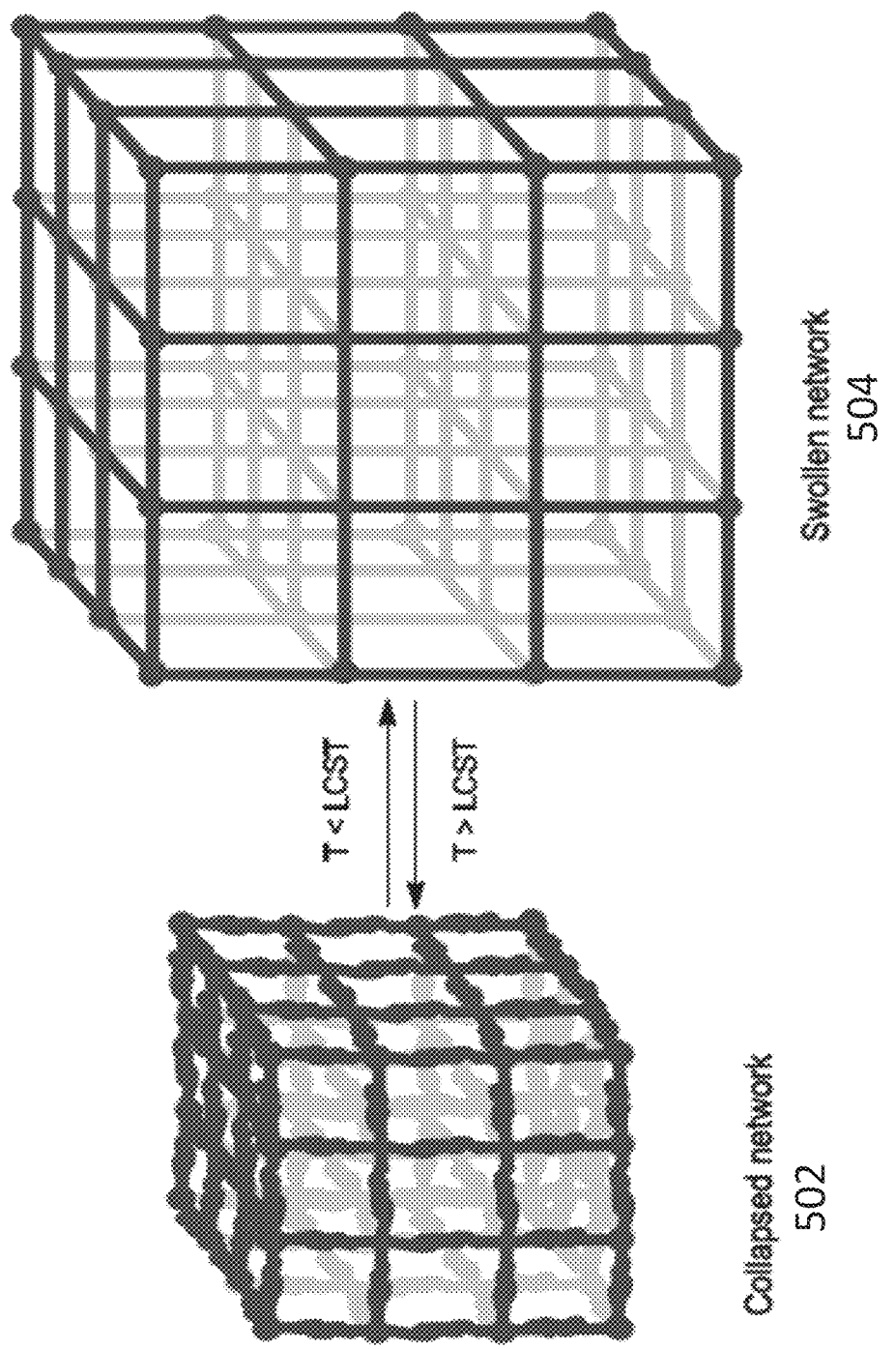
FIG. 5 is a schematic illustration of covalently linked networks, demonstrating the effect of temperature on the swelling of covalently linked networks.

Reference is made to FIG. 5 which schematically illustrates covalently linked networks, demonstrating the effect of temperature on the swelling of covalently linked networks.

As shown in FIG. 5 covalently linked networks, e.g., hydrogel networks, dispersed in water may form semi solid states containing at least 99% water w/w to polymer weight. These gels can be either covalently linked polymer networks or physical gels. With reference to thermoresponsive polymers, covalently linked networks exhibit a change in their degree of swelling in response to temperature whereas physical gels show a sol-gel transition, for example, when the solution temperature is below the LCST, the covalently linked networks will have a swollen network formation 504 and when the solution temperature is raised above the LCST, the covalently linked networks will have a collapsed network formation 502.

Non limiting example of thermoresponsive polymers may be selected from the group consisting of conetworks such as for example PNIPAAm and hydroxyethyl methacrylate (HEMA) copolymer, PNIPAAm-co-PHEMA, and NIPAAm with butyl methacrylate (BuMA), P(NIPAAm-co-BuMA), poly(dimethyl acrylamide) (PDMAAm) with Poly (methoxyethyl acrylate), PDMAAm-co-Poly(methoxyethyl acrylate), PNIPAAm hydrogels with polyamino acid cross-linked chains which are thermoresponsive degradable hydrogels, synthesized elastin like polymers with polypeptide repeat units, biodegradable hydrogel comprising thermoresponsive PNIPAAm with cleavable lactic acid and dextran groups, hydrogels of poly(ethylene glycol) monomethyl ether methacrylate (PEGMA), ABA triblock copolymers of PNIPAAm (block A) and poly(N,N-dimethylacrylamide) (PDMAAm, block B), Conetworks of PNIPAAm, PHEMA and a lactic acid monomer and thermoresponsive cellulose derivatives such as methylcellulose and hydroxypropyl cellulose based hydrogels.

Another group of crosslinked hydrogels are the interpenetrating networks (IPN). Interpenetrating networks, according to International Union of Pure and Applied Chemistry (IUPAC), consist of two covalently linked polymer networks which may be bound together by physical entanglement as opposed to covalent bonds. Specifically, this requires the polymerization of both networks simultaneously and results in two intermixed networks that can only be separated by breaking bonds. These materials are of interest due to their ability to introduce new properties when the networks interact or two different properties when acting independently. For example, an interpenetrating network of polyacrylic acid (PAA) and polyacrylamide (PAAm) forms hydrogels that swell above their upper critical solution temperature (UCST), e.g., due to hydrogen bonding between the two different networks being disrupted at higher temperatures allowing the networks to swell.

Semi interpenetrating networks (SIPN) differ from IPNs in the sense that they are not entwined networks. SIPNs consist of a crosslinked network with linear or branched polymer chains penetrating them. For example, SIPN may be synthesized from crosslinked gellan gum microspheres with interpenetrating PNIPAAm chains. Another example of seminterpenetrating networks is PNIPAAm-co-PAAc with linear PAAc-co-peptide chains that shows degradation properties to be dependent on peptide crosslinks and PAAc-co-peptide concentrations.

Micelles-Forming Block Copolymer

According to some demonstrative embodiments, the composition of the present invention may include at least one micelle-forming block copolymer. According to some embodiments, the micelles-forming polymeric may include amphiphilic di-block (hydrophilic-hydrophobic) or tri-block (hydrophilic-hydrophobic-hydrophilic) polymers.

Compared to surfactant micelles, polymeric micelles are generally more stable, with a remarkably lowered CMC, and have a slower rate of dissociation.

Additional structures may include graft (hydrophilic-g-hydrophobic) or ionic (hydrophilic-ionic) copolymers. In some embodiments, the hydrophilic segment may be composed of poly(ethylene glycol) (PEG). While alternative hydrophilic polymers such as poly(ethylenimine) poly(aspartic acid), poly(acrylic acid), dextran and etc may also be used, hydrophobic or ionic segments are preferred.

The defining characteristic of micelle systems, according to some embodiments of the present invention, is the ability of polymer units to self-assemble into nano-scale aggregates. Self-assembly is a thermodynamic process. The potential for self-assembly is determined by the mass and composition of the copolymer backbone, the concentration of polymer chains, and the properties of fatty component which should be encapsulated into the micelles.

According to some embodiments, amphiphilic polymers may self-assemble in aqueous solutions with the hydrophobic chains aggregating together to form the core and the hydrophilic chains extended towards the aqueous environment. According to these embodiments, the hydrophilic chains shield the hydrophobic chains from interaction with water, reducing the interfacial free energy of the polymer-water system. Minimizing interfacial free energy is the main driving force for micelle formation. In aqueous solutions, the hydrophobic effect is the major mechanism for decreasing interfacial free energy.

Any macromolecule assumes a conformation in solution that is directed by the balance between the strengths of interaction of the polymer segments between themselves and with the solvent molecules. This balance is generically called solvent quality and has been assessed by a variety of parameters of which the most commonly used are the Hildebrand solubility parameter δ and the Flory parameter X. According to the first approach, a good solvent would present a solubility parameter (which reflects its cohesive energy) closer to that of the macromolecule, whereas within Flory theory, the smaller (or more negative) the Flory parameter, the more favorable the monomer-solvent interaction.

In addition, the size of the macromolecule may play an important role in defining its solution conformation due to a configurational entropy contribution, which is most commonly assessed through lattice analysis, as proposed by Flory.

For a block copolymer, this balance becomes more complex to include contributions from the interactions of two building blocks. A rare situation would be when these interactions involve a solvent that is good for one of the units but poor for the other(s). This situation represents what is called a selective solvent, being selective to the block whose solvation is more intense. This situation, consequently, leads to an amphiphilic behaviour and, therefore, to a tendency to the copolymer self-assembly similar to surfactant solutions. According to some embodiments, these copolymers may act as very effective surface active agents, being used in many applications for their interfacial activity.

Figure 7:
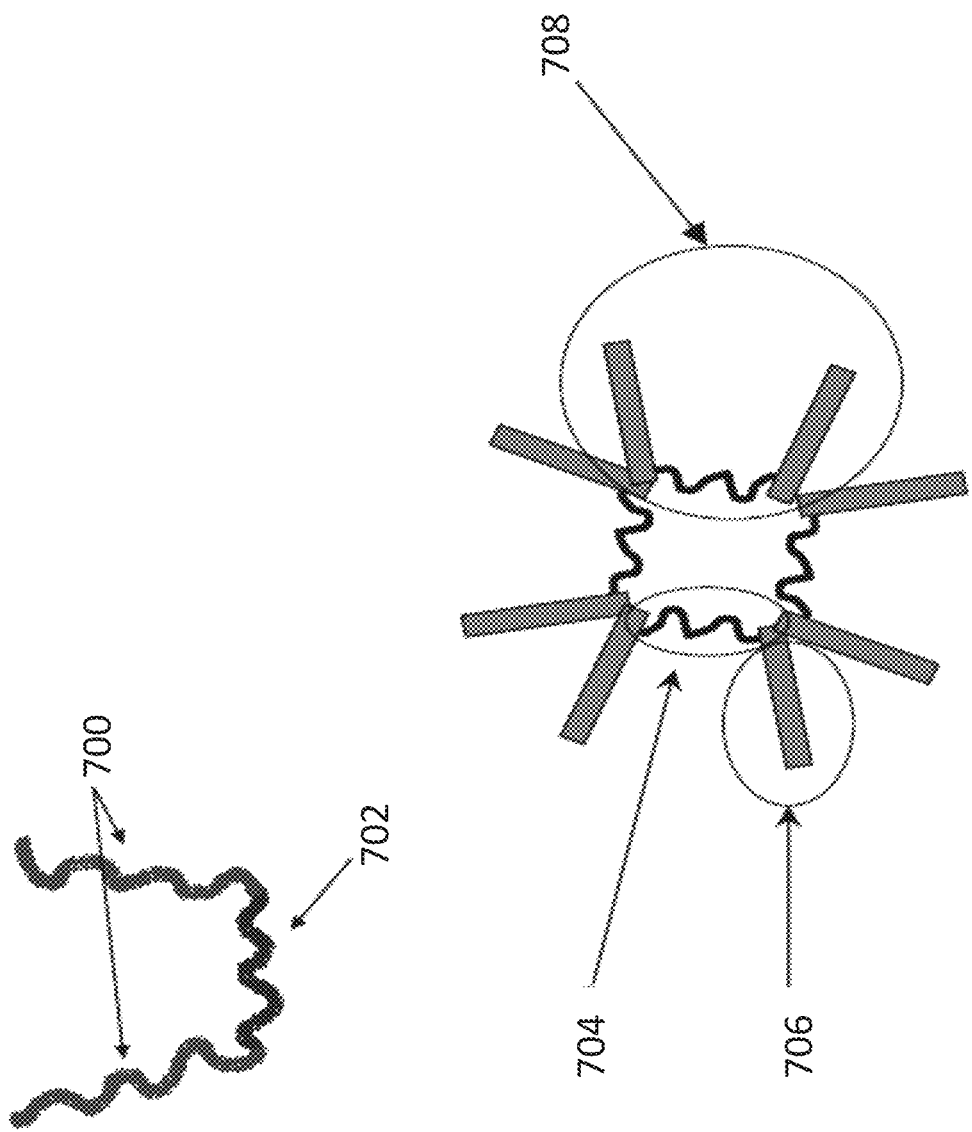
FIG. 7 is a schematic illustration of a specific micelle-forming triblock-copolymer and the structure of a micelle composed of micelle-forming block copolymer according to some demonstrative embodiments described herein.

The self-assembling may produce structures of the same kind as those verified in normal surfactant solutions, generically called micelles (possibly including a variety of shapes) and mesophases (possibly involving different geometry and arrangements), as depicted for example in FIGS. 1 and 7.

Some differences, however, may be found in terms of nomenclature for association processes involving these macromolecules with respect to their similarity with normal surfactants. The first one involves the initial state, where no association occurs, which for low-molecular-weight surfactants is associated with the term monomers. With block copolymers, this term would cause confusion with the macromolecule building units. Hence, the non-aggregated state is referred to as unimers. Sometimes, e.g., especially for copolymers with large insoluble blocks, liophobic sites are formed due to compact coiling of these units even at the non-aggregated state, generating what is known as "unimolecular micelles". However, it is to be noted that according to some embodiments of the present invention, the term "micelle" as used herein may refer to any form of aggregate of surfactant molecules dispersed in a liquid colloid. The micelles of the present invention may be in a form a spheres, ellipsoids, cylinders, unilayers, bilayers and the like. The micelles of the present invention may also be lack of any defined regular shape. According to some embodiments in normal surfactant solutions, micelles would be aggregates that are stable in a significant range of environmental conditions (e.g., concentration, temperature, and presence of additives) as to produce an aggregate with constant aggregation number, size, and shape. For block copolymer solutions, the aggregation process may be significantly more complex. In some demonstrative embodiments, the composition of present invention may include non-ionic and/or ionic copolymer aggregates formed in water, in non-aqueous solvents and/or in supercritical fluids. Moreover, a series of examples is described herein to represent the wide range of pssible applications involving the important aggregates of the present invention.

The critical micelle concentration (CMC) is the minimum concentration of polymer required for micelles to form. At low polymer concentrations, there are insufficient numbers of chains to self-assemble and instead the chains are found distributed throughout the solution and act as surfactants, adsorbing at the air-water or aqueous-organic solvent interface. As the concentration of polymer increases, more chains are adsorbed at the interface. Eventually a concentration is reached at which both the bulk solution and interface are saturated with polymer chains—this is referred to as the CMC. Adding more polymer chains to the system beyond this point will result in micelle formation in the bulk solution to reduce the free energy of the system. At high polymer concentration, the micelles are stable unless they are diluted below the CMC. The micelles will then disassemble and free chains are again found in the bulk solution and adsorbed at the air-water interface or aqueous-organic solvent interface.

While micelles are often pictured as spheres, according to some embodiments, the micelles are not always spherical and not solid particles. The individual polymer chains that form a micelle may be in dynamic equilibrium with chains that remain in the bulk solution, at the solvent interface, and incorporated into adjacent micelles.

The structure, molecular weights and molar mass ratio between hydrophilic and hydrophobic segments of the polymer backbone have a direct impact on the size and shape of assembled micelles. In general, according to some embodiments, when the hydrophilic polymer segment (corona) is longer than the hydrophobic polymer segment (core), spherical micelles are favored; however, an increase in the number of crystalline folds in the core leads to a reduction in corona crowding, favoring rod-like morphologies.

As micelles are physically assembled structures, environmental changes may often result in size changes and therefore impact micelle stability. In addition, micelle size may be determined by the molecular geometry of the individual chains which may be influenced by solution conditions such as ionic strength, pH, temperature, and polymer concentration.

In some demonstrative embodiments of the present invention, for example, for use in the sealing film, micelles should preferably remain intact during formulation and administration to contain the fatty component of the film. The stability of micelles can be thought of generally in terms of thermodynamic and kinetic stability. Thermodynamic stability describes how the system acts as micelles are formed and reach equilibrium. Kinetic stability describes the behavior of the system over time and details the rate of polymer exchange and micelle disassembly.

The CMC is a fundamental parameter used to characterize the thermodynamic stability of micelles. It is related to thermal energy, $k_B T$, and the effective interaction energy between polymers and the bulk solution, $\varepsilon_h$, in the equation, $CMC=\exp(-n\varepsilon_h/k_B T)$. Lower values indicate greater thermodynamic stability. CMC is also directly related to the standard free energy of micellization, $\Delta G°_{mic}$, in the equation, $\Delta G°_{mic}=RT \ln(CMC)$. According to some embodiments, polymeric micelles exhibit lower CMC values than low molar mass surfactant micelles because the polymer chains have many more points of interaction than small molecules. Polymer solutions exhibit different physical properties below and above the CMC. Typically, polymeric micelle CMCs are at micro-molar concentrations. The length of the hydrophobic segment correlates directly with stability. The propensity for micelles to dissociate is related to the composition and cohesion of the hydrophobic core. According to some embodiments, increasing the hydrophobicity of the copolymer increases the cohesion of the hydrophobic core and results in a lower CMC.

According to some embodiments, an interaction between the fatty component of the micelle and the material encompassed within the core of the micelles may also affect and/or compromise stability. Generally, an encapsulated, hydrophobic component may stabilize the micelle through additional hydrophobic interactions between the core and the fatty component.

Thermodynamic stability may be also influenced by the interactions between polymer chains in the corona with each other and with the aqueous environment. Some micelles of the present invention may employ PEG as the hydrophilic segment. According to some embodiments, individual PEG chains interact by intermolecular van der Waals forces; the PEG chains interact with water in the bulk solution by hydrophilic interactions, such as hydrogen bonding/dipole-dipole forces. In some embodiments, increasing the PEG chain length and surface density may force the polymers to adopt more rigid and extended, e.g., brush-like conformations. In contrast, low MW PEG and low surface density of PEG may result in limited surface coverage of the micelle, leading to aqueous exposure to the hydrophobic core and micelle destabilization. Sufficient hydrophilic polymer surface coverage is required to allow fluid movement of surface chains while also preventing exposure of the hydrophobic core.

For block copolymer micelles, increased hydrophobic chain length generally correlates with increased stability (and therefore reduced CMC).

According to some preferred embodiments, there is a balance between the hydrophobic and hydrophilic chain lengths on the copolymer, e.g., for achieving maximum stability. Beyond a certain point, increasing the hydrophobic chain length leads to micelles of less uniform shape, resulting in non-spherical aggregates. In addition to the length of the hydrophobic block, the hydrophobicity of the core may also influence micelle stability. According to some demonstrative embodiments, the most hydrophobic copolymer has the lowest CMC. Increased hydrophobicity and stacking interactions in the core may decrease the CMC. In contrast, according to some embodiments, micelles formed from mixtures of two hydrophobic copolymer chains may have much higher CMCs. Therefore the hydrophobicity alone is insufficient to predict stability, and that intermolecular interactions in the micelle core, such as stacking interactions, resulted in a "glassy" state in the core can influence stability as well.

According to some demonstrative embodiments of the present invention, the composition including the hydrophobic chain may be paramount in micelle design. In some embodiments, increasing the hydrophobic chain length and/or degree of hydrophobicity may lead to more stable micelles. e g., as described in detail below.

Kinetic Stability

Kinetic stability describes the behavior of the micelle system over time in aqueous solution, specifically dealing with the dynamics between individual micelles, their environment and each other. Any change in the environment of a micelle may impact stability. As vehicles for entrapping fatty component in the hybrid film, micelles are exposed to extreme and acute changes in their environment. After micellization, individual chains remain dynamic and exchange between micelles and the bulk solution. Finally, after being exposed to changes in the environment or by simple dilution, or spraying the emulsion formulation for coating granules or microspheres micelles may begin to fall apart. Therefore, kinetic stability is used to describe the dynamics of micelles over time and during the process of disassembly. It is essential to characterize the kinetic stability of micelles to ensure that the encapsulated fatty component cargo is not released prematurely.

At equilibrium, the concentration of individual polymer chains (A) with respect to the concentration of micelles may be described as shown below:

$$K_M=[A]^n/[\text{micelle}]$$

$K_M$ is the micelle dissociation constant and has the units of concentration and n is the aggregation number of the micelle.

The dynamic equilibrium for copolymer exchange in micelles can be classified into three distinct mechanisms as follows; chain insertion/expulsion, micelle merging/splitting, and micelle spanning. For chain expulsion and insertion, a polymer chain is expelled from one micelle, returns to the bulk, and is then inserted into a second micelle. Chains can be exchanged when two micelles temporarily merge and the micellar cores come in contact. Here, the chain transfers from the first micelle to the second. The final mechanism for copolymer exchange occurs by micellar spanning. The exteriors of two micelles may be bridged by one extended chain without the chain ever completely returning to the bulk. The chain migrates from one micelle to another in this manner without being completely expelled from a micelle and without the two micelle cores ever contacting.

In general the Kinetic stability is dependent on CMC, Tg, block ratios, and the encapsulated fatty component.

Increasing the hydrophobic lengths in block copolymers may result in increased kinetic stability.

Another important characteristic value for any surfactant is the Hydrophilic/Lipophilic Balance (HLB) value, i.e., the ratio of the hydrophobic portion to the hydrophilic portion. This balance is based on molecular weight of each portion. In general it applies to nonionic surfactants only. The HLB value is an indication of the solubility of the surfactant. The lower the HLB value the more lipophilic or oil soluble the surfactant is. On the contrary, the higher the HLB value the more water soluble or hydrophilic the surfactant is. This surfactant solubility property is an indicator of its likely end use. HLB value is the molecular weight percent of the hydrophilic portion of the nonionic surfactant divided by five. This number is a relative or comparative number and not a mathematical calculation.

The micelles forming block copolymers according to the present invention have an HLB value of about 9 to 20.

Block Copolymer Micelles in Water

Water is unique in terms of its properties as solvent, which arise from a singular cohesive energy due to the strongest hydrogen bridging network among polar solvents. Surface activity and tendency to self-assembly is displayed when a dissolved molecule presents an apolar moiety attached to polar (ionic or nonionic groups), due to its dual interaction with water. The most common polar group found in aqueous block copolymer micelles is poly(ethylene oxide), attached to a variety of apolar moieties. The simplest a polar group is a long hydrocarbon chain, as found in normal nonionic surfactants.

Poly(ethylene oxide) (PEO), also called poly(ethylene glycol) (PEG), most commonly when referring to oligomers, is highly soluble in water, and its strong hydration is due to a very favorable fitting of the ethylene oxide monomer into the water structure. An important feature of its solution behavior is that EO hydration is strongly temperature dependent, producing a upper critical solution temperature (UCST) behavior. The Flory-theta temperature for PEO in water is close to 100° C., and solution cloud points above this temperature have been reported. Two nonexclusive proposals have been put forward to explain PEO water UCST behavior: The first ascribes PEO decreased solubility to less efficient hydration due to decreased hydrogen bonding and the second ascribes the phenomenon to the attainment of PEO less polar configurations, which are statistically more significant and would become more populated at higher temperatures. The important consequence is that PEO aqueous solubility and, therefore, of its block copolymers, may be tuned by temperature variations, providing an alternative way (in addition to concentration changes) to varying its self-assembling. In fact, similar temperature effects on solubility are also displayed by aqueous solutions of other nonionic polymers, [e.g., poly(N-isopropyl acrylamide) (NIPA), poly(lactic acid), hydrophobically modified celluloses, among others]. As a general picture, these copolymers aggregationis favored both by increases in temperature and concentration.

In addition, the formation of higher-order aggregates (or mesophases) follows the same trend, leading, eventually to polymer phase separation.

Out of the many PEO-containing block copolymers, the most commonly used according to the present invention are those belonging to the family of Poloxamer (Pharmacopoeial name), PEO-PPO-PEO block copolymers [PPO standing for poly(propylene oxide)] which is a family of ABA-type tri-block copolymer consisting of more than 30 non-ionic amphiphilic copolymers.

These are low-cost, biocompatible copolymers that may display varied solution behavior, depending on their PEO-PPO ratio and polymer molecular weight. Because PO is only slightly soluble in water at room temperature, the PEO-PPO ratio controls the polymer solubility (or its HLB, hydrophilic-lipophilic balance, value), hence driving its most suitable application.

In industry, they are usually referred to by their trade names [e.g., Pluronics® (BASF), Lutrol Kolliphor, or Synperonics (ICI)]. These copolymers are available in molecular weights ranging from 1000 to 15,000 Da, and with PEO-PPO ratios between 10 and 80 wt % of PEO. Their aqueous solubility and association behavior, as well as their performance in specific applications are strongly dependent on these parameters. The many manufacturers use different codes, but these usually indicate the PEO content (the last digit 10=PEO wt %) and size of the PPO middle group (proportional to the first digits). The general chemical structure of this block copolymer has been shown below as its molecular weight and PEO-PPO ratios have been calculated for both Poloxamer 188 and Poloxamer 407.

Poloxamer Chemical Composition:

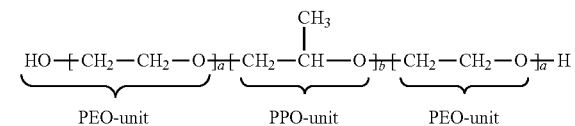

| Pharmacopoeial name | | | Trade Name |
|---|---|---|---|
| Poloxamer 188 | a = ca. 80 | b = ca. 27 | Lutror ® F 68 |
| Poloxamer 407 | a = ca. 101 | b = ca. 56 | Lutror ® F 127 |

Likewise the Table below shows the PEO-PPO ratios for different kinds of Poloxamer;

| Poloxamer | a | b |
|---|---|---|
| 124 | 12 | 20 |
| 188 | 80 | 27 |
| 237 | 64 | 37 |
| 338 | 141 | 44 |
| 407 | 101 | 56 |

The character of each poloxamer in terms of molecular weight, appearance (liquid, solid paste), hydrophilicity/hydrophobicity and solubility may be determined by the chain length of the polyoxyethylene (PEO) units and polyoxypropylene (PPO) units.

Copolymer aggregation may be directed by changes in either concentration or temperature or both. According to some embodiments, there is provided a process for producing the composition as described herein, In some embodiments, the process may include a first aggregation step, from unimers to micelles, wherein the concentration at which micelles start to appear isdefined as the critical micelle concentration (cmc), likewise to normal surfactants. Similarly, the temperature at which, for a given polymer concentration, micelles are formed, is called critical micelle temperature (cmt).

The cmc and cmt values may be obtained by using a variety of techniques, similar to investigations with normal surfactants. Among some of the most commonly used methods are surface tension measurements [which usually present more than one break point, solubilization of apolar dyes or spectroscopic probes, including absorption, fluorescence measurements, light-scattering Techniques, NMR spectroscopy, DSC (usually high sensitivity DSC), and scanning densitometry; these last two techniques are appropriate only for cmt determination, whereas the other apply to both cmc and cmt measurements.

According to some embodiments, the sizes and radius of the copolymer micelles described herein may remain fairly constant as the copolymer concentration increases, but they generally increase as temperature is raised.

According to some embodiments, some generalization may be attempted to relate cmc values (which are directly related to the Gibbs energy of micelle formation, through $\Delta_{mic}G=RT \ln \text{cmc}$) to features of the copolymer composition, more often its EO and PO content as expressed in the following equation;

$$\text{Ln(cmc/mol L}^{-1})=(1/RT)[-7.68-0.0016 N_{EO}-0.150 N_{PO}]$$

where NEO and NPO are the number of EO and PO segments in the polymer molecule.

A similar approach can be applied regarding cmt values using the following equation;

$$\text{cmt}=(N_{EO}+N_{PO})(R \ln X)^{-1} \times [1000 \, M_w^{-1}(0.367 \log C-1.255)-0.0045 \log C-0.0070]$$

Although limited by the complexity of the aggregation phenomena, these equations may be useful to predict copolymer aggregation state at certain concentration and temperature.

In some demonstrative embodiments, there may be a dominant role for the hydrophobic PO units on the aggregation process. In addition, different from low molecular-weight of the surfactants for which an increase of the EO chain would lead to an increase in cmc due to increased surfactant solubility, for EO-PO-EO block copolymers, according to some embodiments, the EO contribution may be quite small, if not negligible. This may occur due to a counterbalance of a contribution from increase in solubility as the EO chain increases, and an opposite one from configuration entropy, since the polymer chain becomes larger and more difficult to arrange in solution. The enthalpy of micellization can be determined by the following relationship using a high-sensitivity DSC at 0.5% copolymer solutions.

$$\Delta_{mic}H=\text{kJ mol}^{-1}=117.6-0.187 N_{EO}+3.25 N_{PO}$$

where NEO and NPO are the number of EO and PO units per polymer molecule.

This behavior was interpreted in terms of the dehydration of the hydrophobic PO units (since data for phase separation of pure PPO conforms to the same relationship), which was then identified as the key step in the aggregation process. Although significant structural changes may be observed at higher temperatures due to formation of higher order aggregates or mesophases, and, ultimately, at phase separation, manifested by the so called cloud point, enthalpy changes at those events are much smaller. One explanation for this finding is that the most energetic step, PO dehydration, was already accomplished at the first aggregation stage. After this, the other structural changes would only involve changes of copolymer packing and not an extensive EO dehydration. Since copolymer aggregation is associated with an enthalpy increase (endothermic process), it must be driven by a larger entropy increase, attributed to the release of water molecules involved in polymer (mostly PO units) solvation, which is a general behavior for aggregation of low-molecular-weight surfactants in water. Accordingly, the other phase transitions are also associated with enthalpy increase, although smaller, and should be also entropy driven.

In terms of block composition, EO units have little effect, as already mentioned; hence, the aggregation is controlled by the hydrophobic block. Therefore, the molecular architecture of these copolymers, and especially that of hydrophobic block, can significantly affect their aggregation behavior. Assessing the contributions of different blocks as the change in cmc caused by the addition of one hydrophobic unit, it is possible to compare their relative hydrophobicity.

According to some embodiments, other block copolymers which are able to form micelles are di-blocks of EO-PO and EO-B and tri-block versions, PO-EO-PO and BO-EO-BO (BO; butylenes oxide). The latter are, sometimes, called reverse block copolymers, since their end groups are hydrophobic, in contrast to those with EO as end groups. Because association in water is obtained via these end groups, this may cause an additional entropic barrier, due to constraints related to the curving the macromolecule chain and, hence, their micellization is less favorable (cmc values are about one order of magnitude higher) than that of diblock and EO-X-EO copolymers.

In general, these mostly spherical block copolymer micelles are larger than the ones formed by low molecular weight surfactants.

For EO-PO-EO block copolymers at 40 to 50° C. (far from their cloud points), these spherical micelles contain between 15 and 60 molecules per aggregate, with hydrodynamic radii in the range of 6 to 10 nm, and may be values of the same order of magnitude for EO-BO-EO block copolymers.

Besides spherical micelles, other arrangements are known to be formed by these EO-PO-EO copolymers, typically at higher concentrations and temperatures, ranging from cylinders or rods, in cubic or hexagonal arrangements, lamellae, and other structures. Aggregation of these copolymers in water is sensitive to the presence of many additives, for example the addition of salting-out electrolytes, (e.g., NaCl) may decrease both cmc and cmt values, whereas organic solvents as small alcohols and salting-in compounds (e.g., urea) may have the opposite effect.

The same behavior may also be observed for the cloud points of these copolymer aqueous solutions in the presence of these additives. The most striking effects may be observed with the addition of ionic surfactants (especially anionic). Addition of sodium dodecylsulfate (SDS) to copolymer solutions may lead to successive decrease in signs of micelle formation, until complete disappearing.

Micelles-Forming Ionic Block Copolymers

The presence of electrical charges in the block copolymer molecule adds new features to an already complex aggregation process. In general, the same trends observed for nonionic block copolymers, which are controlled by an amphiphilic behavior due to solvent selectivity, are displayed by solutions of ionic block copolymers. In addition, owing to a higher incompatibility between the ionic and nonionic (usually hydrophobic) blocks, these aggregates may start to form at very low concentrations, hence presenting low cmc values (as low as $10^{-8}$ mol L$^{-1}$) and, consequently, high stability. These low cmc values are sometimes difficult to measure, being close to the detection limits of some techniques, requiring, sometimes, indirect approaches based on the fit of experimental data to theoretical models.

Depending on the solvent selectivity, these aggregates are classed as block ionomers or block polyelectrolytes. The former occurs in organic solvents, where the ionic moieties form the core of the aggregate, surrounded by the apolar blocks, in a way similar to the formation of reverse micelles by low molecular weight surfactants; in fact, this terminology also applies to macromolecular surfactants as these block copolymers. The other arrangement, with the core composed by the noionic blocks and the micelle corona containing the ionic blocks is verified in water or mixtures of water and a polar organic solvent (like methanol).

Another division is based on the arrangement of these chains in solution, mostly affected by their relative sizes and stretching due to solvation, leading to two limit cases, known as star and crew-cut micelles. The spherical star micelles may be composed of a small core and large corona region, associated with relatively smaller insoluble blocks. The latter regime is found when the copolymer presents a large nonionic block and a short ionic moiety. Block polyelectrolytes may assemble in both regimes, whereas for block ionomers, crew-cut micelles have not been observed yet.

One very striking difference when comparing block copolymer aggregates to those formed by small surfactants refers to the kinetics of macromolecule exchange between micelle and solution. In some cases, when the insoluble block presents high Tg (glass transition temperature) glassy cores are formed, causing an extremely low chain mobility, sometimes making it difficult to attain equilibrium conditions, hence preventing the application of some thermodynamic models and scaling approaches. One representative example is a di- and triblock poly(methacrilic acid)/poly(styrene), PMA/PS, copolymers in water dioxane mixtures. When prepared in dioxane-rich mixtures, a dynamic equilibrium between micelles and unimers was found, but as the aggregates were transferred to a water-rich environment via dialysis, frozen micelles behaving like autonomous particles were detected.

Example of micelle-forming block copolymers, according to the present invention, may be selected from the group consisting of di or triblock copolymers such as, for example, but not limited to Poloxamers which are a group of poly (ethylene oxide)-poly (propylene oxide)-poly (ethylene oxide) triblock copolymers (PEO-PPO-PEO) (Pluronics®, Lutrol®, Kolliphor® or Syneronics®), poly (propylene oxide)-poly (ethylene oxide)-poly (propylene oxide) triblock copolymers (PPO-PEO-PPO), poly (butylene oxide)-poly (ethylene oxide)-(butylene oxide) triblock copolymers (PBO-EO-PBO), poly (ethylene oxide)-poly (butylene oxide)-poly (ethylene oxide) triblock copolymers (PEO-PBO-PEO), Poly(ethylene oxide)-Poly(butylene oxide) diblock copolymer, Poly(ethylene oxide)-Poly(propylene oxide) diblock copolymer, Poly(ethylene-alt-propylene)-poly(ethylene oxide) diblock copolymer, poly(ethylene oxide)-poly(styrene) diblock copolymer, poly(ethylene oxide)-poly(D,L-lactide) diblock copolymer, poly(ethylene oxide)-poly(ε-caprolactone) diblock copolymer, poly(ethylene oxide)-poly(hydrocarbon chain) diblock copolymer, poly(styrene)-poly(vinylpyridine) block copolymers, Poly (ethylene oxide) poly(ethyelene imine) block copolymers, Poly(styrene)-poly(vinyleriphenylphosphine), block copolymers of polyamino acid-PEO copolymers with hydrophobic blocks of aspartic acid and aspartate derivatives, polylysine, polycaprolactone, and poly(lactide), polication-PEO copolymers containing, e.g., poly(ethyleneimine), ionic block copolymers such as polystyrene(PS)-b-polyacrylic acid (PAA), polystyrene(PS)-b-poly(methacrylic acid) (PMA), poly(styrene)-poly(ethylene-propylene) (PS-PEP) diblock and triblock copolymers, poly(styrene)-b-poly(ethylene-butylene) (PS-PEB) diblock and triblock copolymers, poly(styrene)-b-poly(t-butylstyrene) (PS-PtBS) diblock and triblock copolymers, poly(styrene)-poly(hydrogenated polybutadiene)-poly(styrene) (PS-PHB-PS) triblock copolymers, poly(styrene)-poly(isoprene)-poly(styrene) PS-PI-PS triblock copolymers, poly(styrene)-poly (1,1-dihydroperfluorooctyl acrylate) (PS-PFOA), block copolymers of triblock polyalkylene oxide such as poly(dimethylsiloxane)-polyalkylene oxide block copolymers, poly(vinyl acetate)-poly(1,1-dihydroperfluorooctyl acrylate) block copolymers, polycarbolactone-polyethylene glycol polycarbolactone (PCL-PEG-PCL) triblock copolymer, poly(ethylene glycol)-diblock-polycaprolactone (PEG-b-PCL) copolymer, 1,2-distearoyl-phosphatidyl ethanolamine-PEG (2000) (DSPE-PEG2000), poly(ethylene oxide)-block-poly(N-hexyl-Laspartamide) (PEO-b-p(N-HA), poly(ethylene glycol)-poly(aspartic acid) (PEG-P[Asp(ADR)]), PEG-block-poly (N-hexyl stearate L-aspartamide) (PEG-b-PHSA), poly(DL-lactide-co-2-methyl-2-carboxytrimethylene carbonate)-graft-PEG (poly(LA-co-TMCC)-g-PEG), PEG-poly(benzyl aspartate) block-copolymer, PEG-block poly(glutamic acid) PEG-b-poly(Glu), polysorbates (Tween) such as Polysorbate 20 (Polyoxyethylene and sorbitan monolaurate), Polysorbate 40 (Polyoxyethylene and sorbitan monopalmitate), Polysorbate 60 (Polyoxyethylene and sorbitan monostearate), Polysorbate 80 (Polyoxyethylene and sorbitan monooleate), Polyoxyethylene and sorbitan tristearate, poly-d,l-lactide-coglycolide(PLGA) and polyethylene glycol block copolymer Hydrophobic Fatty Component The most suitable materials which can act as an appropriate hydrophobic fatty component according to the present invention are alkenes, waxes, esters, fatty acids, alcohols, and glycols, each with varying performance and properties independent of each other. Example of materials that may be used as hydrophobic fatty component is selected from the group consisting of alkenes such as paraffin wax which is composed of a chain of alkenes, normal paraffins of type $C_nH_{2n+2}$ which are a family of saturated hydrocarbons which are waxy solids having melting point in the range of 23-67° C. (depending on the number of alkanes in the chain); both natural waxes (which are typically esters of fatty acids and long chain alcohols) and synthetic waxes (which are long-chain hydrocarbons lacking functional groups) such as bee wax, carnauba wax, japan wax, bone wax, paraffin wax, chinese wax, lanolin (wool wax), shellac wax, spermaceti, bayberry wax, candelilla wax, castor wax, esparto wax, jojoba oil, ouricury wax, rice bran wax, soy wax, ceresin waxes, montan wax, ozocerite, peat waxes, microcrystalline wax, petroleum jelly, polyethylene waxes, fischer-tropsch waxes, chemically modified waxes, substituted amide waxes; polymerized α-olefins; hydrogenated vegetable oil, hydrogenated castor oil; fatty acids, such as lauric acid, myristic acid, palmitic acid, palmitate, palmitoleate, hydroxypalmitate, stearic acid, arachidic acid, oleic acid, stearic acid, behenic acid, sodium stearat, calcium stearate, magnesiu stearate, hydroxyoctacosanyl hydroxystearate, oleate esters of long-chain, esters of fatty acids, fatty alcohols, esterified fatty diols, hydroxylated fatty acid, hydrogenated fatty acid (saturated or partially saturated fatty acids), aliphatic alcohols, phospholipids, lecithin, phosphathydil cholin, triesters of fatty acids for example triglycerides received from fatty acids and glycerol (1,2,3-trihydroxypropane) including fats and oils such as coconut oil, hydrogenated coconut oil, cacao butter (also called *Theobroma* oil or *Theobroma cacao*); eutectics such as fatty acid eutectics which are a mixture of two or more substances which both possess reliable melting and solidification behaviour; and a combination thereof.

Blend polymer can also be used as an appropriate hydrophobic fatty component. The blend can be either miscible or immiscible where the former generally results only in one melting point whereas the latter may show separated melting points attributed to the pure fatty component.

EXAMPLES

Abbreviations

LCST—Lower Critical Solution Temperature
FNP—Film Forming Polymer
MFP—Micelles Forming Polymer
MP—Melting point
Sol: Solution
FA—Fatty Acid
HPC—Hydroxypropyl cellulose
PVA—Polyvinyl alcohol
OA—Oleic Acid
SA—Stearic Acid
MA—Myristic Acid
BA—Behenic Acid
EtOH—Ethanol
MP—Melting Point
O/W—Oil in Water Emulsion
Material List
FNP: HPC or a polymeric blend comprising HPC and PVA
MFP: Pluronic F127
FA: OA, SA, MA, BA
Organic solvent: Ethanol
Specifications
LCST of FFP>LCST of MFP
40° C.<LCST of FFP<70° C.
MP of FA>LCST of MFP
Melt Method Reference is now made to FIG. 6 is a schematic illustration of a melt method for preparing a film composition according to some demonstrative embodiments described herein.

Figure 6:
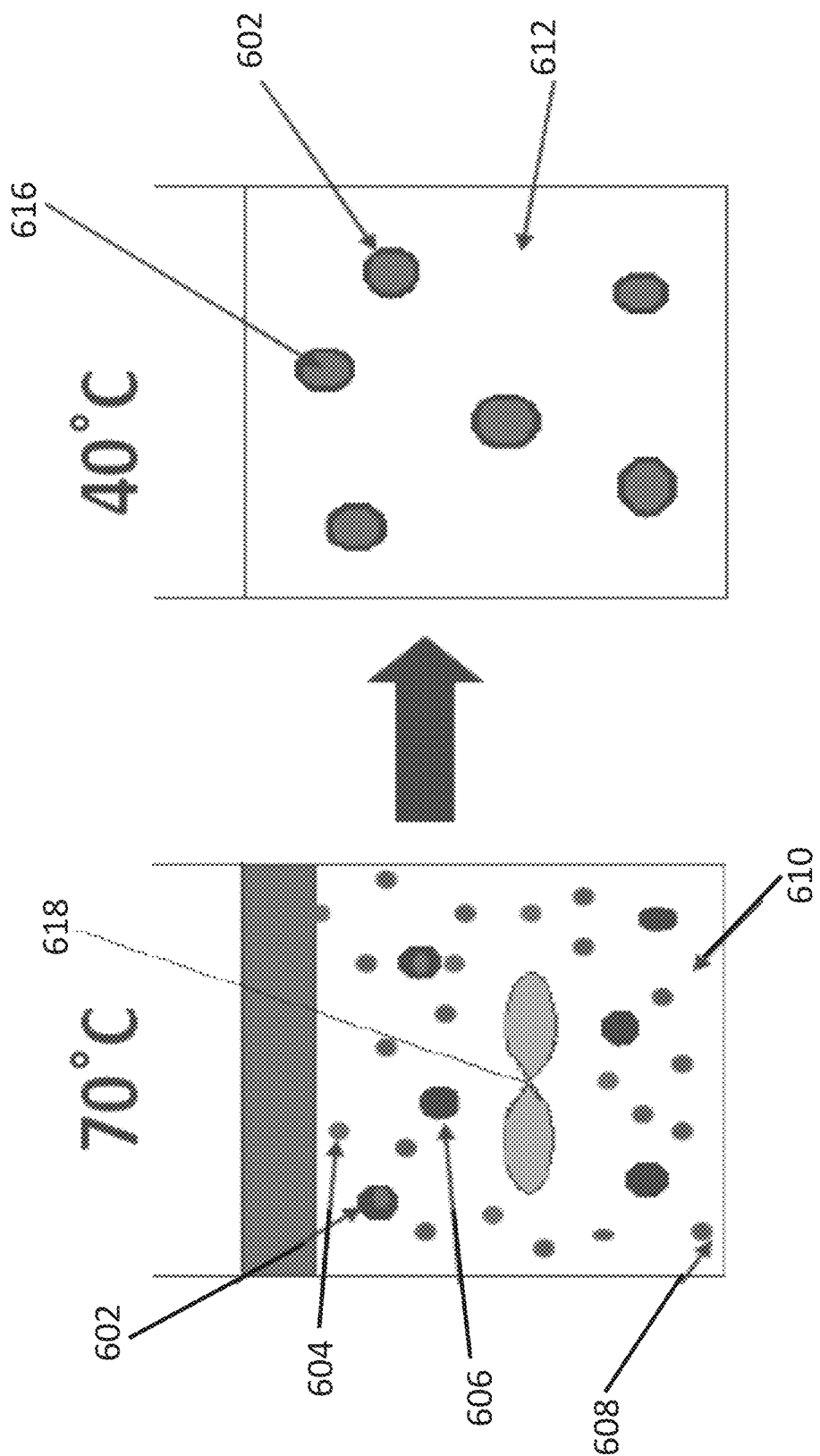
FIG. 6 is a schematic illustration of a melt method for preparing a film composition according to some demonstrative embodiments described herein.

FIG. 6 illustrates a melt method for preparing a film composition containing hydrophilic film forming polymer, micelles forming block copolymer and a hydrophobic fatty component. In the method there is provided a base suspension, where via elevating the temperature above a certain point, e.g., above the LCST, a resulting suspension is formed.

As shown in FIG. 6, based on this method there is first provided a base aqueous suspension 610 of hydrophilic film forming polymer comprising Hydroxypropyl cellulose (HPC) particle 608, Pluronic® particle 606, liquid Fatty Acid (FA) 604 and a few Pluronic® encapsulated fatty acid particles 602. The suspension is placed in a receptacle with a homogenizer 618, e.g., a high shear homogenizer.

The base suspension is exposed to a temperature higher than its LCST, e.g., 70° C. as shown in FIG. 6, and then a melt of both micelles forming block copolymer and a hydrophobic fatty component is added into the suspension while high agitation using a high shear homogenizer.

After the temperature is lowered, e.g., to 40° C. as shown in FIG. 6, the resulting solution is comprised of HPC aqueous solution 612 which includes mainly Pluronic® encapsulated fatty acid particles 602, having a core of solid FA 616.

Reference is now made to FIG. 7 which is an example of specific micelle formation.

As shown in FIG. 7, a micelle-forming block copolymer according to the present invention may have a PEO 700 and a PPO 702. According to some demonstrative embodiments, upon formation of the micelle, the micelle structure may include at least one micelle-forming block copolymer (poloxamer) 708 comprising POP group 704 and at least one POE group 706.

Figure 8:
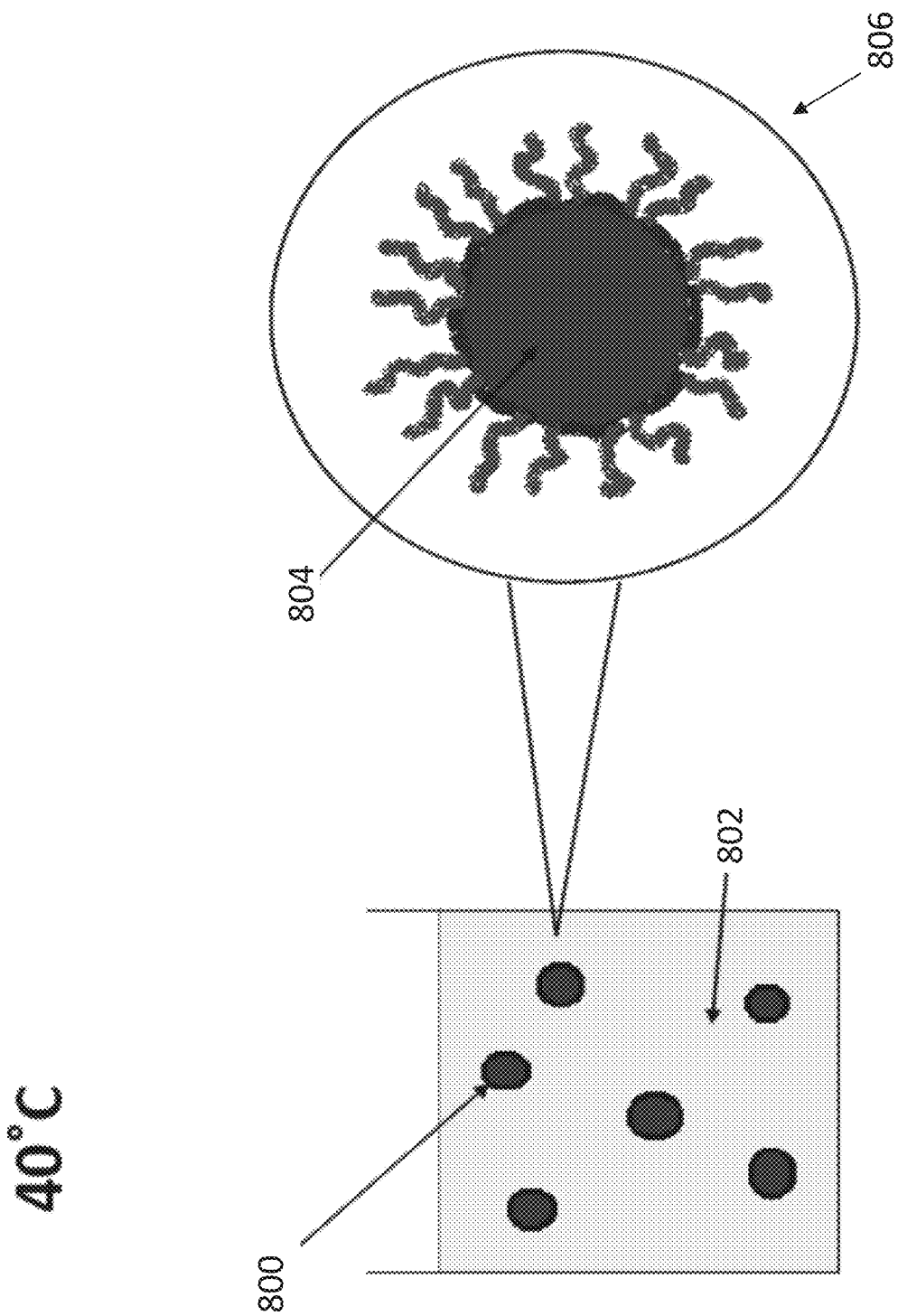
FIG. 8 is a schematic illustration of a micelle structure according to some demonstrative embodiments described herein.

Reference is now made to FIG. 8 which is a schematic illustration of a Pluronic® encapsulated fatty acid particles 800 in an HPC aqueous solution 802, and an enlarged view of a micelle structure 806 (Pluronic® micelle), having a solid FA core 804. According to some embodiments, micelle structure 806 may contain the hydrophobic fatty component formed in melt method in the hydrophilic film forming polymer solution at a temperature below LCST of hydrophilic film forming polymer and above LCST of the micelles forming block-copolymer and at a concentration above its CMC.

Example 1—Melt Method (A)

Figure 9:
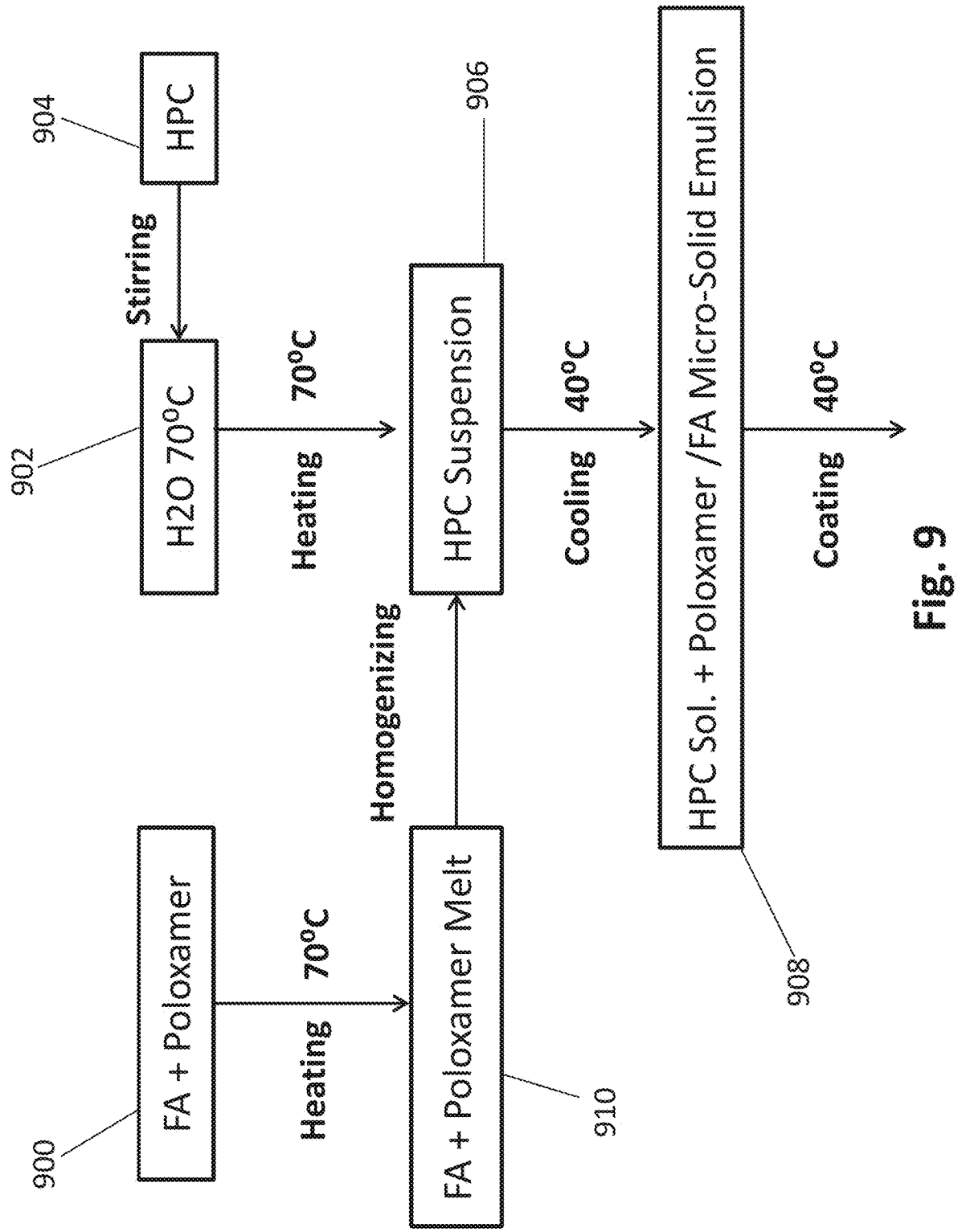
FIGS. 9 and 10 demonstrate a block diagram illustrating a preparation process of a suspension for coating process based on a melt method according to some demonstrative embodiments described herein.

Reference is made to FIG. 9, which illustrates an exemplary preparation process of a suspension for coating process based on a melt method, according to the present invention, comprising hydroxypropyl cellulose (HPC) as hydrophilic film forming polymer, Poloxamer as a micelle forming block-copolymer and a fatty acid (FA) as a hydrophobic fatty component.

As shown in block 904 HPC is stirred with $H_2O$ at 70° C. of block 902.

As shown in block 900, FA and Poloxamer may undergo heating at 70° C. to provide an FA and Poloxamer as shown in block 910. Melt 910 undergoes homogenization and mixed with the solution of block 902 to provide an HPC suspension 906.

The suspension 906 is cooled to 40° C. to provide an HPC Solution and Poloxamer/FA Micro-Solid Emulsion as shown in block 908, which may be used for coating at 40° C.

Example 2—Melt Method (B)

Figure 10:
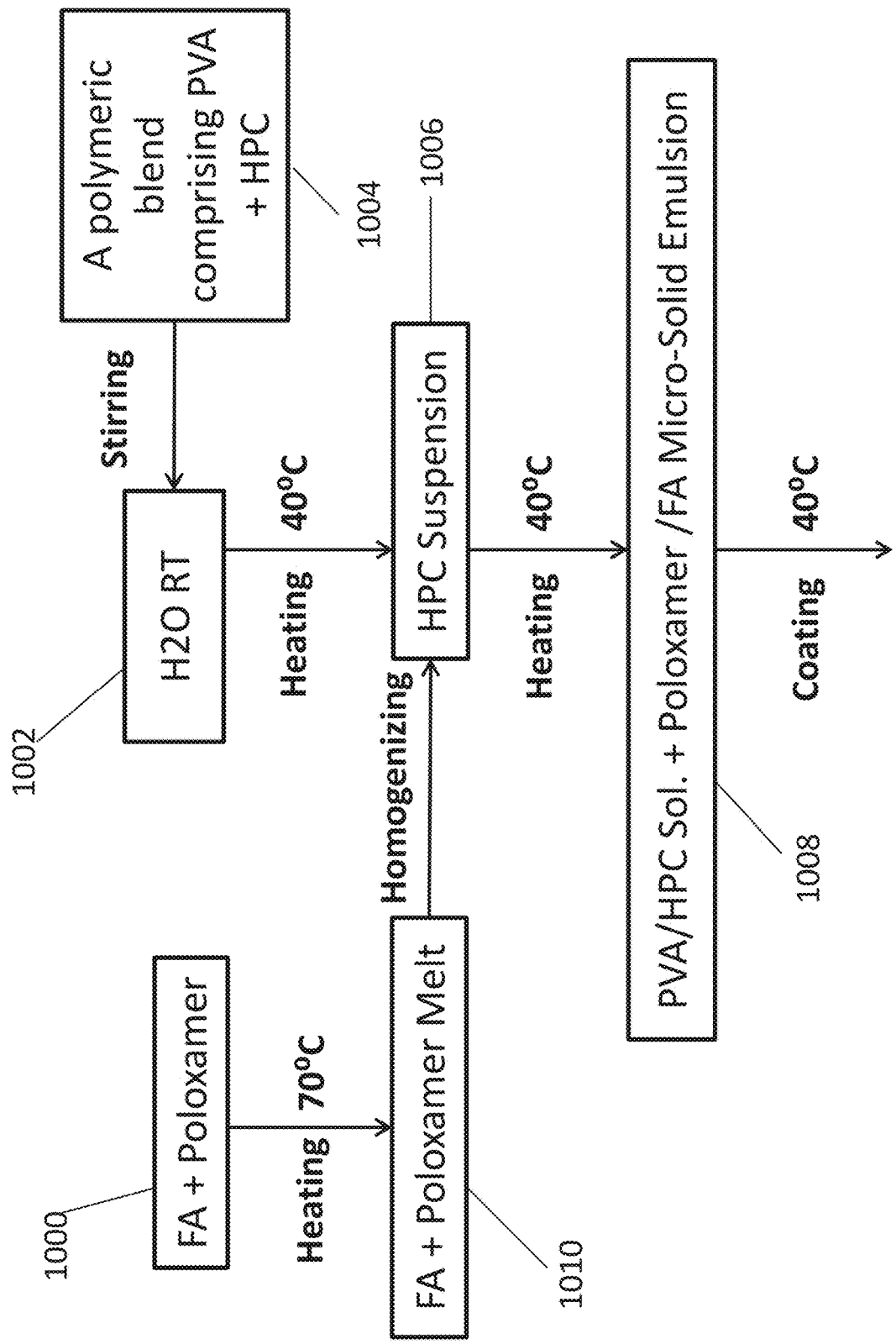

Reference is made to FIG. 10, which illustrates an exemplary preparation process of a suspension for coating based on a melt method, according to the present invention, comprising a polymeric blend comprising hydroxypropyl cellulose (HPC) and polyvinyl alcohol (PVA) as hydrophilic film forming polymer, Poloxamer as a micelle forming block-copolymer and a fatty acid (FA) as a hydrophobic fatty component.

As shown in block 1004 A polymeric blend comprising PVA+HPC is stirred with $H_2O$ at room temperature (RT), of block 1002.

As shown in block 1000, FA and Poloxamer may undergo heating at 70° C. to provide an FA and Poloxamer as shown in block 1010. Melt 1010 undergoes homogenization and mixed with the solution of block 1002, which is preheated to 40° C., to provide an HPC suspension 1006.

The suspension 1006 is further heated at 40° C. to provide an HPC Solution and Poloxamer/FA Micro-Solid Emulsion as shown in block 1008, which may be used for coating at 40° C.

Example 3—Organic Solution Method

Figure 11:
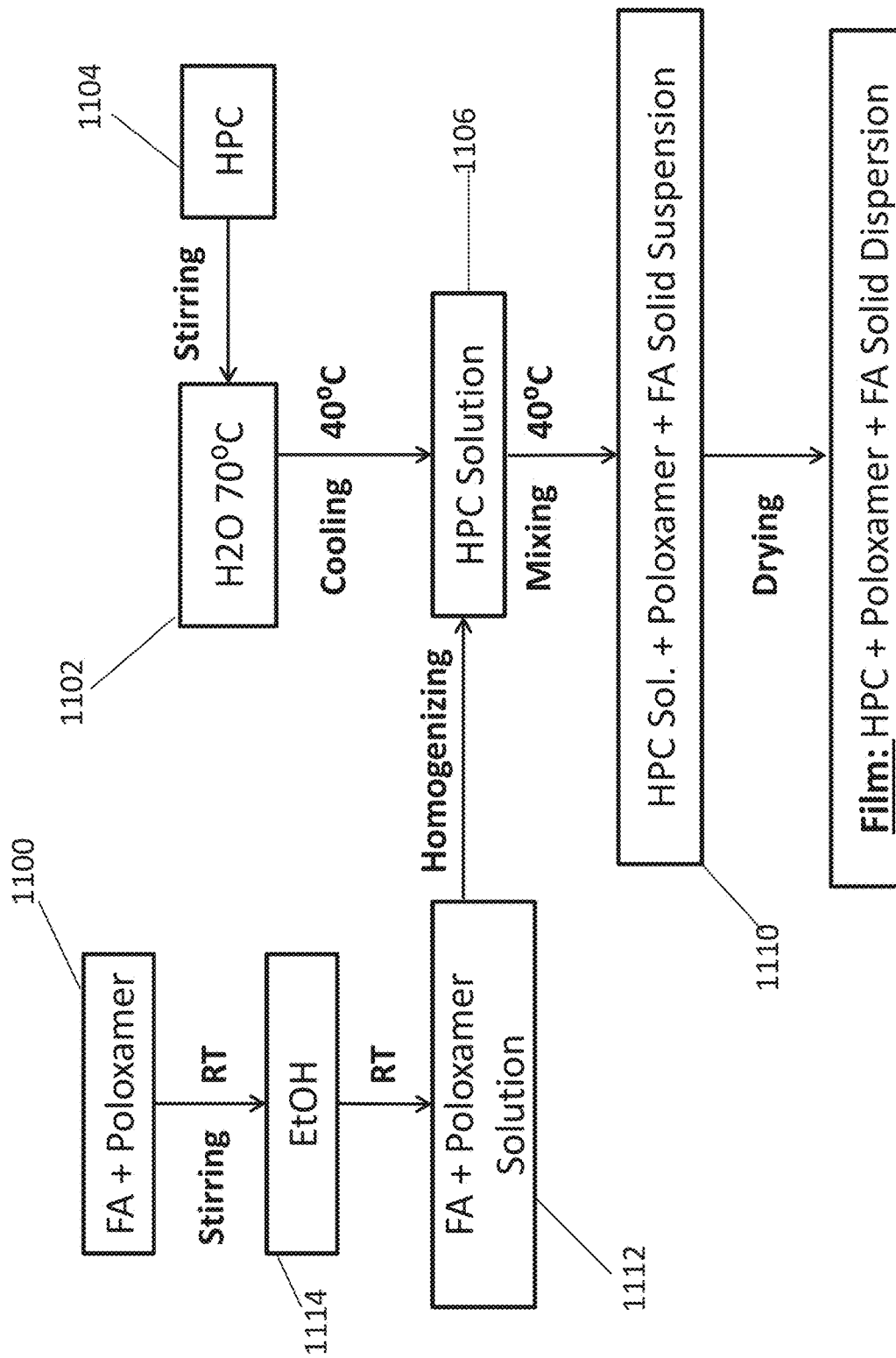
FIGS. 11 and 12 demonstrate a block diagram illustrating the preparation process of a suspension for coating process based on an organic solution method according to some demonstrative embodiments described herein.
Figure 12:
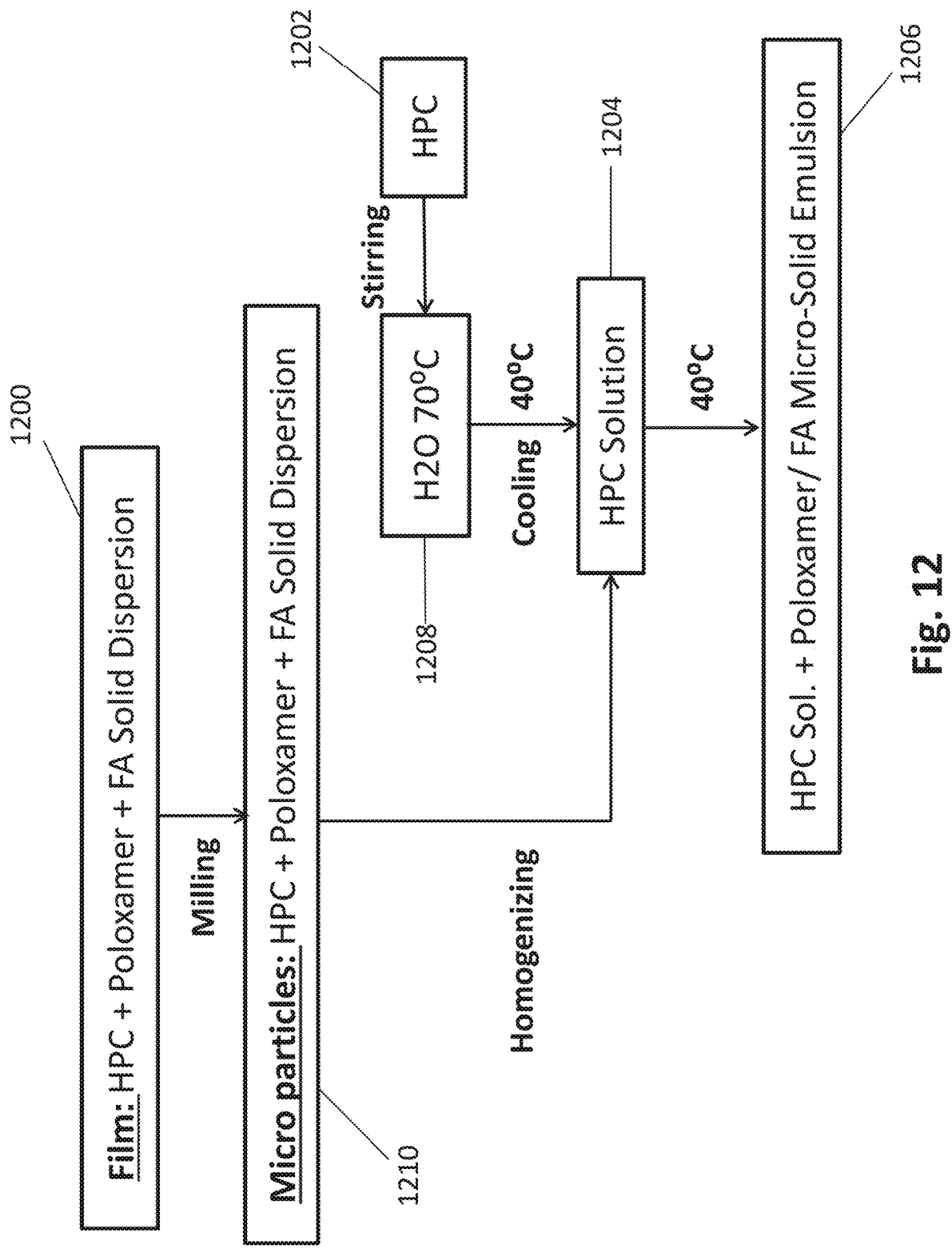

Reference is made to FIGS. 11 and 12, which illustrate n exemplary preparation process of a suspension for coating process based on an organic solution method, according to some embodiments of the present invention. According to some embodiments the process comprising hydroxypropyl cellulose (HPC) as hydrophilic film forming polymer, Poloxamer as a micelle forming block-copolymer and a fatty acid (FA) as a hydrophobic fatty component. With reference to FIG. 11, as shown in block 1104 HPC is stirred with $H_2O$ at 70° C. of block 1102.

As shown in block 1100, FA and Poloxamer may undergo stiffing at room temperature and mixed with EtOH, block 1114, at room temperature to yield FA and Poloxamer as shown in block 1112. Melt 910 undergoes homogenization and mixed with the solution of block 1102 to provide an HPC solution 1106.

The solution 1106 is mixed at 40° C. to provide an HPC Solution and Poloxamer+FA Solid Suspension as shown in block 1110. The suspension of block 1110 is then dried to yield a film 1108 which contains HPC+Poloxamer+FA Solid Dispersion.

With reference to FIG. 12, as shown in block 1200, which is equivalent to block 1108 of FIG. 11, film containing HPC+Poloxamer+FA Solid Dispersion undergoes milling to provide micro particles 1210 containing HPC+Poloxamer+FA Solid Dispersion.

As shown in block 1202 HPC is stirred with $H_2O$ at 70° C. of block 1208.

Micro particles 1210 undergo homogenization and are mixed with the solution of block 1208 (which is cooled to a temperature of 40° C.). to provide an HPC solution 1204.

The HPC solution 1204 is further mixed at a temperature of 40° C. to provide an HPC solution+Poloxamer/FA Micro-Solid Emulsion 1206.

Figure 13:
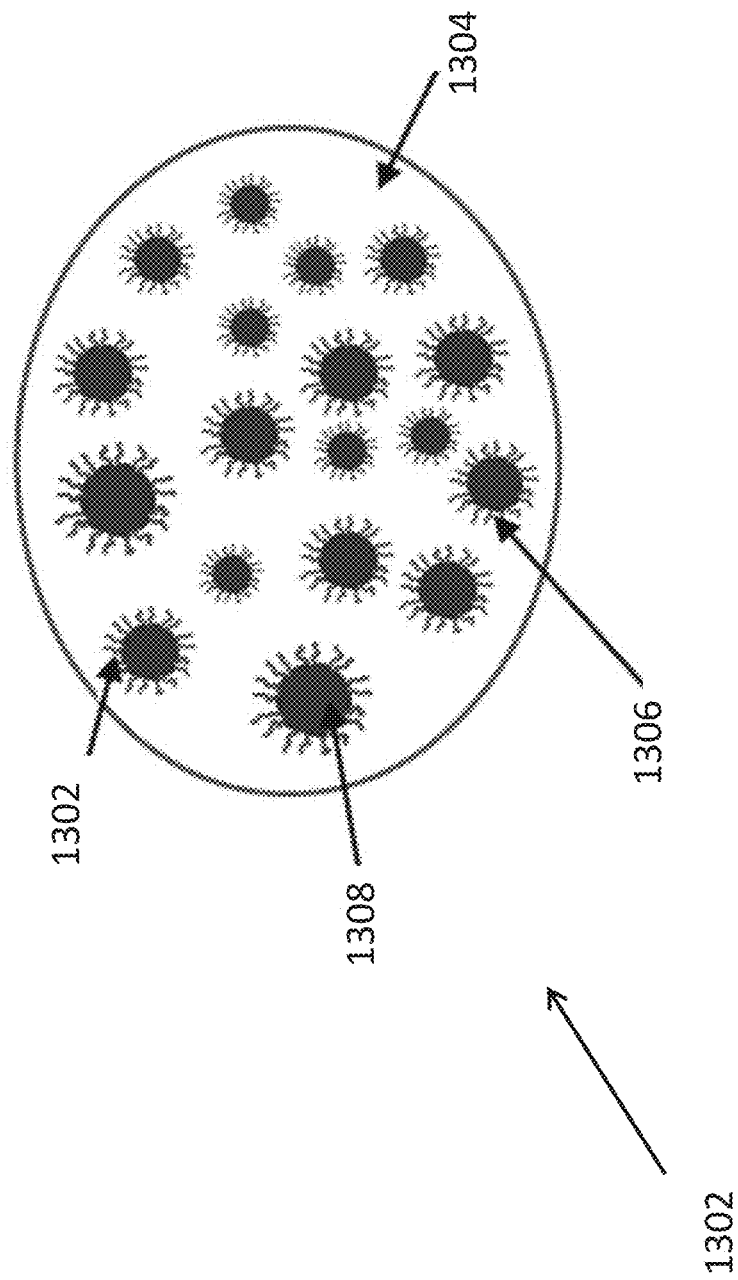
FIG. 13 is a schematic illustration of a film composition according to some demonstrative embodiments described herein.

Reference is now made to FIG. 13, which is a schematic illustration of a film composition 1302 according to some embodiments of the present invention, comprising hydrophilic film forming polymer in which hydrophobic fatty component is molecularly blended by a microstructure of micelles using a micelle forming block-copolymer.

As shown in FIG. 13, film 1302 includes a Pluronic® Micelle 1302 having a Solid FA core 1308 and a Pluronic® Encapsulated FA 1306, dispersed in an HPC matrix film 1304.

Example 4—Oil Solution Method

Figure 14:
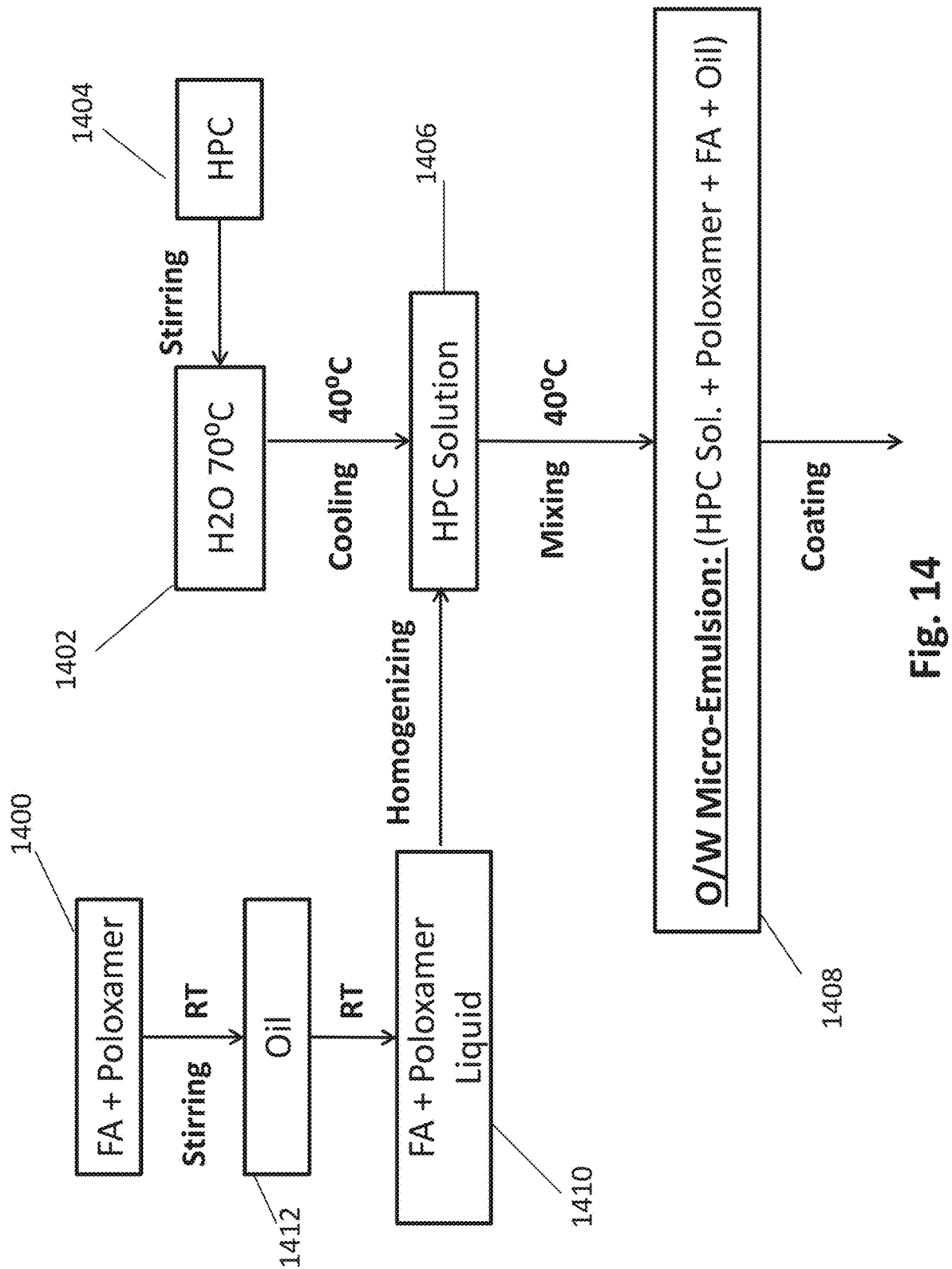
FIG. 14 demonstrates a block diagram illustrating the preparation process of a suspension for coating process based on an oil solution method according to some demonstrative embodiments described herein.

Reference is made to FIG. 14, which illustrates an exemplary preparation process of a suspension for coating process based on an oil solution method, according to the present invention, comprising hydroxypropyl cellulose (HPC) as hydrophilic film forming polymer, Poloxamer as a micelle forming block-copolymer and a fatty acid (FA) as a hydrophobic fatty component.

As shown in block 1404 HPC is stirred with $H_2O$ at 70° C., of block 1402.

As shown in block 1400, FA and Poloxamer liquid as shown in block 1410. FA and Poloxamer liquid of block 1410 undergoes homogenization and mixed with the solution of block 1402, which is cooled to 40° C., to provide an HPC solution 1406.

The solution 1406 is further mixed at 40° C. to provide an Oil in Water (o/w) Micro-Emulsion 1408, which contains HPC Solution and Poloxamer and FA and oil. The O/W Micro-Emulsion 1408 may be used for coating.

While this invention has been described in terms of some specific examples, many modifications and variations are possible. It is therefore understood that within the scope of the appended claims, the invention may be realized otherwise than as specifically described.

What is claimed is:

1. A film composition comprising micelles dispersed in said film composition, for coating a pharmaceutical, nutraceutical or nutritional composition comprising a molecular mixture of:

a hydrophilic film forming polymer having thermo-sensitive sol gel forming properties and having a first lower critical solution temperature (LCST), a hydrophobic fatty component in free form entrapped within said micelles, wherein said hydrophobic fatty component is selected from the group consisting of waxes and fatty acids;

a micelle-forming block copolymer having a second lower critical solution temperature (LCST) and an HLB value of about 9 to 20, wherein said block copolymer comprises one or more of a poly (propylene oxide)-poly (ethylene oxide)-poly (propylene oxide) PEO-PPO-PEO block copolymer; and wherein said second LCST is higher than said first LCST; and wherein said film composition is a matrix film in a dry form.

2. The composition of claim 1, wherein said hydrophilic film forming polymer comprises one or more of poly-N-substituted acrylamide derivative, polypropyleneoxide, polyvinylmethylether, partially-acetylated product of polyvinyl alcohol, Methylcellulose (MC), hydroxylpropylcellulose (HPC), methylhydroxyethylcelluloce (MHEC), hydroxylpropylmethylcellulose (HPMC), hydroxypropylethylcellulose (HPEC), hydroxymethylpropylcellulose (HMPC), ethylhydroxyethylcellulose (EHEC) (Ethulose), hydroxyethylmethylcellulose (HEMC), hydroxymethylethylcellulose (HMEC), propylhydroxyethylcellulose (PHEC), hydrophobically modified hydroxyethylcellulose (NEXTON), amylose, amylopectin, Poly(organophosphazenes), xyloglucan, synthetic elastin derivative proteins and any of the above polymers further substituted with a hydrophilic or hydrophobic monomer.

3. The composition of claim 2, wherein said poly-N-substituted acrylamide derivative comprises one or more of poly(N-isopropylacrylamide) (PNIPAM), Poly-N-acryloylpiperidine, poly(N,N-diethylacrylamide) (PDEAAm), poly(N-vinlycaprolactam) (PVCL), poly[2-(dimethylamino) ethyl methacrylate] (PDMAEMA), poly(ethylene glycol) (PEG), poly(ethylene oxide) (PEO), PEG methacrylate polymers (PEGMA), Poly-Npropylmethacrylamide, Poly-N-isopropylacrylamide Poly-N-diethylacrylamide, Poly-N-isopropylmethacrylamide, Poly-N-cyclopropylacrylamide, Poly-Nacryloylpyrrolidine, Poly-N,N-ethylmethylacrylamide, Poly-Ncyclopropylmethacrylamide, Poly-N-ethylacrylamide, poly-N-substituted methacrylamide derivatives, copolymers comprising an N-substituted acrylamide derivative and an N-substituted methacrylamide derivative, and a copolymer of N-isopropylacrylamide and acrylic acid.

4. The composition of claim 2, wherein said hydrophilic monomer comprises one or more of N-vinyl pyrrolidone, vinylpyridine, acrylamide, methacrylamide, N-methylacrylamide, hydroxyethylmethacrylate, hydroxymethylacrylate, hydroxyethylacrylate, hydroxymethylmethacrylate, methacrylic acid and acrylic acid having an acidic group, and salts of these acids, vinylsulfonic acid, styrenesulfonic acid, N,N-dimethylaminoethylmethacrylate, N,N-diethylaminoethyl methacrylate, N,N-dimethylaminopropylacrylamide, and salts thereof.

5. The composition of claim 2, wherein said hydrophobic monomer comprises one or more of ethylacrylate, methylmethacrylate, and glycidylmethacrylate; vinylchloride, acrylonitrile, styrene, vinyl acetate.

6. The composition of claim 1, wherein said micelle-forming block copolymer is present at a concentration that is at least a critical micelle concentration (CMC) of said micelle-forming block copolymer.

7. The composition of claim 1, wherein said micelle-forming block copolymer is selected from a poloxamer block copolymer series consisting of Poloxamer 124, Poloxamer 188, Poloxamer 237, Poloxamer 338, and Poloxamer 407 or a combination thereof.

8. The composition of claim 1, wherein said waxes comprise one or more of bee wax, carnauba wax, japan wax, bone wax, paraffin wax, Chinese wax, lanolin (wool wax), shellac wax, spermaceti, bayberry wax, candelilla wax, castor wax, esparto wax, jojoba oil, ouricury wax, rice bran wax, soy wax, ceresin waxes, montan wax, ozocerite, peat waxes, microcrystalline wax, petroleum jelly, polyethylene waxes, fischer-tropsch waxes, chemically modified waxes, substituted amide waxes.

9. The composition of claim 1, wherein said hydrophobic fatty component comprises one or more fatty acids selected from the group consisting of lauric acid, myristic acid, palmitic acid, palmitate, palmitoleate, hydroxypalmitate, arachidic acid, oleic acid, stearic acid, behenic acid, sodium stearate, calcium stearate, magnesium stearate, hydroxyoctacosanyl hydroxystearate, oleate esters of long-chain, esters of fatty acids, fatty alcohols, esterified fatty diols, hydroxylated fatty acid, hydrogenated fatty acid, triesters of fatty acids, triglycerides received from fatty acids and fatty acid eutectics.

10. A pharmaceutical, nutraceutical or nutritional composition, comprising a core and the film composition of claim 1 coating said core.

11. The composition of claim 10, wherein said core comprises granules, microspheres, pellets, microcapsules, mini-tablets, tablets, caplets and capsules.

12. The film composition for coating a pharmaceutical, nutraceutical and nutritional composition of claim 1 comprising a molecular mixture of a Poloxamer, a fatty acid and HPC.

13. A pharmaceutical, nutraceutical or nutritional composition, comprising a core comprising an active ingredient, and a coating layered over said core, said coating comprising the film of claim 1.

* * * * *